(12) United States Patent
Alauddin et al.

(10) Patent No.: US 9,901,420 B2
(45) Date of Patent: Feb. 27, 2018

(54) ORTHODONTIC APPLIANCES INCLUDING FERROMAGNETIC SHAPE MEMORY ALLOYS AND METHODS OF ORTHODONTIC TREATMENT USING SAME

(71) Applicant: Ormco Corporation, Orange, CA (US)

(72) Inventors: Sammel Shahrier Alauddin, Rancho Cucamonga, CA (US); Benjamin Mark Nazeck, San Dimas, CA (US)

(73) Assignee: Ormco Corporation, Orange, CA (US)

( * ) Notice: Subject to any disclaimer, the term of this patent is extended or adjusted under 35 U.S.C. 154(b) by 433 days.

(21) Appl. No.: 14/630,200

(22) Filed: Feb. 24, 2015

(65) Prior Publication Data

US 2015/0238281 A1    Aug. 27, 2015

Related U.S. Application Data

(60) Provisional application No. 61/944,315, filed on Feb. 25, 2014.

(51) Int. Cl.
*A61C 7/28* (2006.01)
*A61C 7/00* (2006.01)

(52) U.S. Cl.
CPC .............. *A61C 7/006* (2013.01); *A61C 7/28* (2013.01); *A61C 7/285* (2013.01); *A61C 7/287* (2013.01); *A61C 2201/007* (2013.01)

(58) Field of Classification Search
CPC ............ A61C 7/285; A61C 7/287; A61C 7/34
See application file for complete search history.

(56) References Cited

U.S. PATENT DOCUMENTS 4,015,333 A * 4/1977 Dellinger ................ A61C 7/00
433/23
4,846,681 A * 7/1989 Mourany ............... A61C 7/006
433/11
5,958,154 A    9/1999 O'Handley et al.
6,247,923 B1 * 6/2001 Vashi .................... A61C 7/287
433/10

(Continued)

OTHER PUBLICATIONS

Wada, Taishi et al., Design of FePd spring actuators, Center for Intelligent Materials and Systems, University of Washington, 2003.
Taya, Minoru et al., Design of Torque Actuators Based on Ferromagnetic Shape Memory Alloy Composites, Proc. SPIE, Smart Struct. Mater. 5054, 156-164, 2003.
Gururaja, S. et al., Design of ferromagnetic shape memory alloy composite made of Fe and TiNi particles, Journal of Applied Physics 102, 064910, 2007.

(Continued)

*Primary Examiner* — Ralph Lewis
(74) *Attorney, Agent, or Firm* — Wood Herron & Evans LLP

(57) ABSTRACT

A self-ligating orthodontic bracket for ligating an archwire includes a bracket body defining an archwire slot configured to receive the archwire, a movable member movable relative to the archwire slot, and an actuator coupled to at least one of the bracket body and the movable member. The actuator includes a ferromagnetic shape memory alloy and is configured to move the movable member when exposed to a magnetic field. A method of orthodontic treatment using a self-ligating orthodontic bracket having an archwire slot configured to receive an archwire therein and including a ferromagnetic shape memory includes exposing at least a portion of the orthodontic bracket to a magnetic field such that the ferromagnetic shape memory alloy at least partially transforms to a martensitic phase from an austenitic phase, and at least one of inserting an archwire into the archwire slot and removing an archwire from the archwire slot.

26 Claims, 27 Drawing Sheets

(56) References Cited

U.S. PATENT DOCUMENTS

| | | | | |
|---|---|---|---|---|
| 6,632,088 | B2* | 10/2003 | Voudouris | A61C 7/12 433/18 |
| 7,104,056 | B2 | 9/2006 | Taya et al. | |
| 7,677,887 | B2* | 3/2010 | Nicholson | A61C 7/28 433/11 |
| 8,016,952 | B2 | 9/2011 | Ishida et al. | |
| 8,033,824 | B2 | 10/2011 | Oda et al. | |
| 8,491,303 | B2* | 7/2013 | Seo | A61C 8/0048 433/173 |
| 9,498,302 | B1* | 11/2016 | Patel | A61C 7/006 |
| 2009/0061380 | A1* | 3/2009 | Yamamoto | A61C 7/00 433/24 |
| 2012/0028206 | A1* | 2/2012 | Lopes | A61C 7/287 433/10 |

OTHER PUBLICATIONS

Liang, Yuanchang et al., Model calculation of 3D-phase transformation diagram of ferromagnetic shape memory alloys, Mechanics of Materials 1404, Sep. 21, 2005.

Liang, Yuanchang et al., Magnetic field-induced reversible actuation using ferromagnetic shape memory alloys, Scripta Materialia 48, 1415-1419, 2003.

Nemat-Nasser, Sia et al., Superelastic and cyclic response of NiTi SMA at various strain rates and temperatures, Mechanics of Materials 38, 463-474, 2006.

Kusaka, Masahiro et al., Design of Ferromagnetic Shape Memory Alloy Composites, Journal of Composite Materials vol. 38 No. 12, 1011-1035, Jun. 2004.

* cited by examiner

ORTHODONTIC APPLIANCES INCLUDING FERROMAGNETIC SHAPE MEMORY ALLOYS AND METHODS OF ORTHODONTIC TREATMENT USING SAME

CROSS-REFERENCE TO RELATED APPLICATION

This application claims priority to U.S. Provisional Patent Application Ser. No. 61/944,315 filed Feb. 25, 2014, the disclosure of which is incorporated by reference herein in its entirety.

TECHNICAL FIELD

The invention relates generally to orthodontic appliances and, more particularly, to orthodontic appliances incorporating ferromagnetic shape memory alloys and methods of orthodontic treatment using ferromagnetic shape memory alloys.

BACKGROUND

Orthodontic brackets represent a principal component of all corrective orthodontic treatments devoted to improving a patient's occlusion. In conventional orthodontic treatments, an orthodontist affixes brackets to the patient's teeth and engages an archwire into a slot of each bracket. The archwire applies corrective forces that coerce the teeth to move into correct orthodontic orientation. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket archwire slot. As such, self-ligating orthodontic brackets require manipulation of the movable portion between an opened position, in which the archwire slot is exposed so as to allow the clinician to remove an archwire from the archwire slot and then insert a new archwire into the archwire slot, and a closed position, in which the movable member retains the archwire in the archwire slot to effectuate treatment.

While such self-ligating brackets are generally successful in achieving their intended purpose, there remain some drawbacks. Manipulation of the movable member requires mechanical actuation of the movable member. In this regard, one drawback is that manipulation often requires use of a tool. The clinician may insert a tool, such as a scalar, into direct contact with the orthodontic bracket and apply a direct mechanical force to the movable member to move it from a closed position to an opened position. Not only is a tool often required, depending on the design of self-ligating orthodontic bracket, the tool may be custom made for that particular bracket design. By requiring a custom tool to be used, treatment may become more complex simply because the clinician must keep track of yet another tool to provide proper treatment.

Another drawback is that orthodontic brackets are generally very small mechanical devices. Due to their small size, manipulation of the movable member often requires excellent visual acuity, manual dexterity, and hand-eye coordination. The lack of any single one of these attributes is particularly problematic when a tool is required to manipulate the movable member, because the tool usually must be inserted into a tiny receptacle to unlatch the movable member and to move it to the opened position. In addition, depending on the orthodontic bracket design, opening the movable member may require specialized training, and the clinician's efficiency at manipulating the movable member may be gained only with significant experience with that particular orthodontic bracket. In any case, chair time for the patient may initially be longer until the clinician gains sufficient experience at manipulating the movable member.

Even though successful, in view of the above, utilizing self-ligating orthodontic brackets may require significant initial chair time, specialized equipment, and clinical training, all of which increases treatment costs. Thus, when present, these characteristics act as barriers to widespread adoption and acceptance of new self-ligating orthodontic bracket designs.

There are also other problems associated with self-ligating brackets. For instance, manufacturing self-ligating orthodontic brackets typically requires subsequent assembly of each of the separately manufactured components. Due to their small size, assembling the movable member together with the bracket body may require special tooling, highly trained workers, or both, all of which drives up manufacturing costs.

Self-ligating orthodontic brackets may also exhibit performance issues that are related to the manufacturing tolerances of each of the movable member and the bracket body. The manufacturing tolerances may become problematic when the separately manufactured components are assembled. Following assembly, when the movable member is closed, the bracket body and the movable member collectively form a closed lumen for capturing the archwire. A close fit between the closed lumen and the archwire is believed to be important for achieving excellent rotational control during orthodontic treatment. Yet, to allow the movable member to be assembled with and move relative to the bracket body between the opened and closed positions, there must be some clearance in the manufacturing tolerances between the bracket body and the movable member by design. When the movable member and the bracket body are assembled, these manufacturing tolerances "stack up" to provide a lumen which may vary significantly in its labial-lingual dimension between different brackets made to the same tolerance specification. Therefore, some of the brackets may provide a relatively loose fit while other brackets may provide a relatively tight fit with the same archwire. Variation in the fit of the archwire with different brackets is believed to result in a diminished capacity to control the rotation of some teeth, such as near the finishing stages of orthodontic treatment. While there may be several factors that cause a reduction in rotational control, it is believed that one of the major causes is the loose fit of the archwire within the archwire slot of the bracket when the movable member is closed.

Thus, while self-ligating brackets have been generally successful, manufacturers of such brackets continually strive to improve orthodontic bracket use and functionality. In this regard, there remains a need for self-ligating orthodontic brackets that reduce chair time and/or improved rotational control during orthodontic treatment, such as during the finishing stages thereof.

SUMMARY

The present invention overcomes the foregoing and other shortcomings and drawbacks of orthodontic brackets heretofore known for use in orthodontic treatment. While the invention will be described in connection with certain embodiments, it will be understood that the invention is not limited to these embodiments. On the contrary, the invention includes all alternatives, modifications and equivalents as may be included within the spirit and scope of the present invention.

According to one embodiment of the present invention, a self-ligating orthodontic bracket for ligating an archwire includes a bracket body defining an archwire slot that is configured to receive the archwire, a movable member movable relative to the archwire slot, and an actuator coupled to at least one of the bracket body and the movable member. The actuator includes a ferromagnetic shape memory alloy and is configured to move the movable member when exposed to a magnetic field. In one embodiment, the ferromagnetic shape memory alloy is one of an iron-palladium (FePd) alloy, a nickel-manganese-gallium (NiMnGa) alloy, or a nickel-manganese-aluminum (NiMnAl) alloy.

In one embodiment, the movable member may be movable from an opened position to a closed position, and the actuator may be configured to move the movable member to the closed position when exposed to a magnetic field. In another embodiment, the movable member may be movable from an opened position to a closed position, and the actuator may be configured to move the movable member to the opened position when exposed to the magnetic field.

In one embodiment, the actuator may have a coil spring shape.

In one embodiment, the actuator may rotate the movable member relative to the bracket body when exposed to the magnetic field or may translate the movable member relative to the bracket body when exposed to the magnetic field.

In one embodiment, the orthodontic bracket may also include a locking mechanism configured to secure the movable member in the closed position.

In one embodiment, the movable member may be a double door-like member.

In one embodiment, a self-ligating orthodontic bracket for ligating an archwire includes a bracket body defining an archwire slot that is configured to receive the archwire and a movable member coupled to the bracket body. The movable member includes a ferromagnetic shape memory alloy and is movable relative to the archwire slot when exposed to a magnetic field. The shape memory alloy may be one of a nickel-titanium (NiTi) alloy, copper-aluminum-nickel (CuAlNi) alloy, or a copper-aluminum-manganese (CuAlMn) alloy.

In one embodiment, the movable member may be a layered composite including at least one layer of the ferromagnetic shape memory alloy and at least one layer of a non-ferromagnetic shape memory alloy. In one embodiment, the movable member may be a coiled door member including at least a coiled portion configured to uncoil and form a planar portion that extends at least partially across the archwire slot. In one embodiment, the movable member may be configured to uncoil when exposed to a magnetic field.

In one embodiment, the movable member may have an L-shaped cross-sectional configuration and a planar configuration. The movable member may be configured to change shape between the L-shaped cross-sectional configuration and the planar configuration when exposed to the magnetic field.

In one embodiment, a self-ligating orthodontic bracket for ligating an archwire includes a bracket body defining an archwire slot that is configured to receive the archwire, a movable member coupled to the bracket body and movable relative to the archwire slot, a base member movably coupled to the bracket body, and a locking system for securing the bracket body relative to the base member. The locking system may include a pin of a ferromagnetic shape memory alloy configured to change shape when exposed to a magnetic field. For example, exposing the locking system to a magnetic field may unlock the locking system.

In one embodiment, the locking system may further include a retaining slot having a plurality of enlarged portions separated by straight portions. The enlarged portions may correspond to predetermined fixed orientations between the bracket body and the base member, and the pin may cooperate with a corresponding one of the enlarged portions for each predetermined fixed orientation. For example, the predetermined fixed orientations may correspond to predetermined torque positions.

In one embodiment, the locking system may also include a retaining slot having a plurality of spaced apart notches corresponding to predetermined fixed relative orientations between the bracket body and the base member. In this embodiment, the pin may cooperate with a corresponding one of the spaced apart notches for each predetermined fixed orientation.

In one embodiment, a method of orthodontic treatment using a self-ligating orthodontic bracket having an archwire slot configured to receive an archwire therein and including a ferromagnetic shape memory alloy includes exposing at least a portion of the orthodontic bracket to a magnetic field such that the ferromagnetic shape memory alloy at least partially transforms to a martensitic phase from an austenitic phase, and at least one of inserting an archwire into the archwire slot and removing an archwire from the archwire slot.

In one embodiment, exposing at least a portion of the orthodontic bracket to a magnetic field includes positioning a device capable of producing a magnetic field proximate the orthodontic bracket prior to inserting or removing the archwire from the archwire slot. The orthodontic bracket may include a movable member such that exposing the orthodontic bracket to the magnetic field causes movement of the movable member. In one embodiment, the movable member may move without contact with a tool.

In one embodiment, a method of orthodontic treatment using a self-ligating orthodontic bracket having an archwire slot that is configured to receive an archwire therein and that includes a ferromagnetic shape memory alloy includes exposing at least a portion of the orthodontic bracket to a magnetic field such that the ferromagnetic shape memory alloy at least partially transforms to a martensitic phase from an austenitic phase and manipulating the orthodontic bracket to change the torque on the tooth. The orthodontic bracket may include a bracket body that is pivotably coupled to a base member and manipulating the orthodontic bracket may include changing the angular orientation between the bracket body and the base member.

In one embodiment, a hand-held dental tool includes at least one of a permanent magnet or an electromagnet configured to produce at least one of a magnetic field or magnetic field gradient for use in exposing the actuator to the magnetic field or the magnetic field gradient.

BRIEF DESCRIPTION OF THE DRAWINGS

The accompanying drawings, which are incorporated in and constitute a part of this specification, illustrate embodiments of the invention and, together with the detailed description given below, serve to explain the invention.

DETAILED DESCRIPTION

Figure 1:
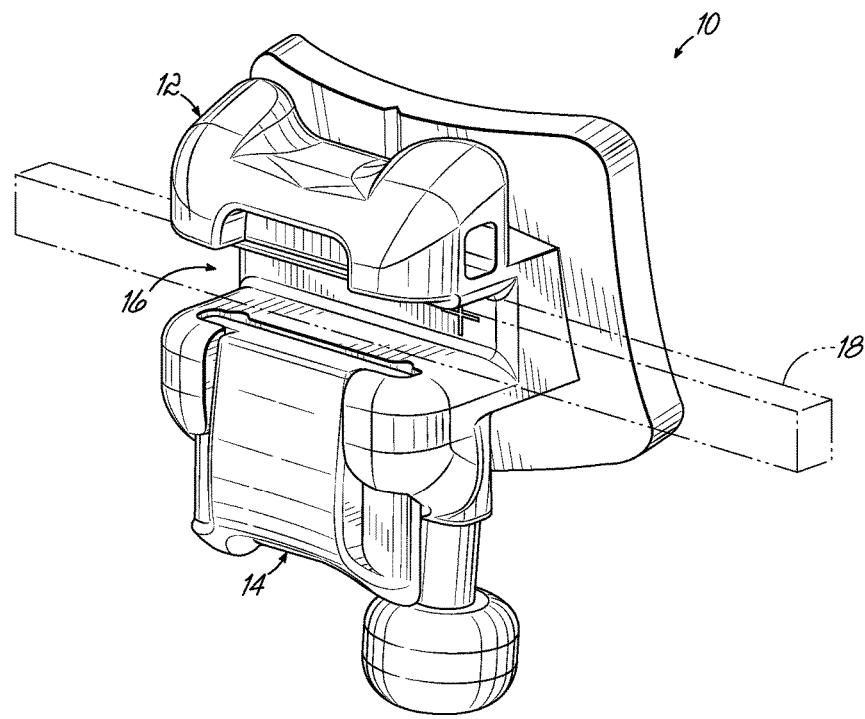
FIG. 1 is a perspective view of an exemplary orthodontic bracket known in the art with a movable member shown in the opened position.
Figure 2:
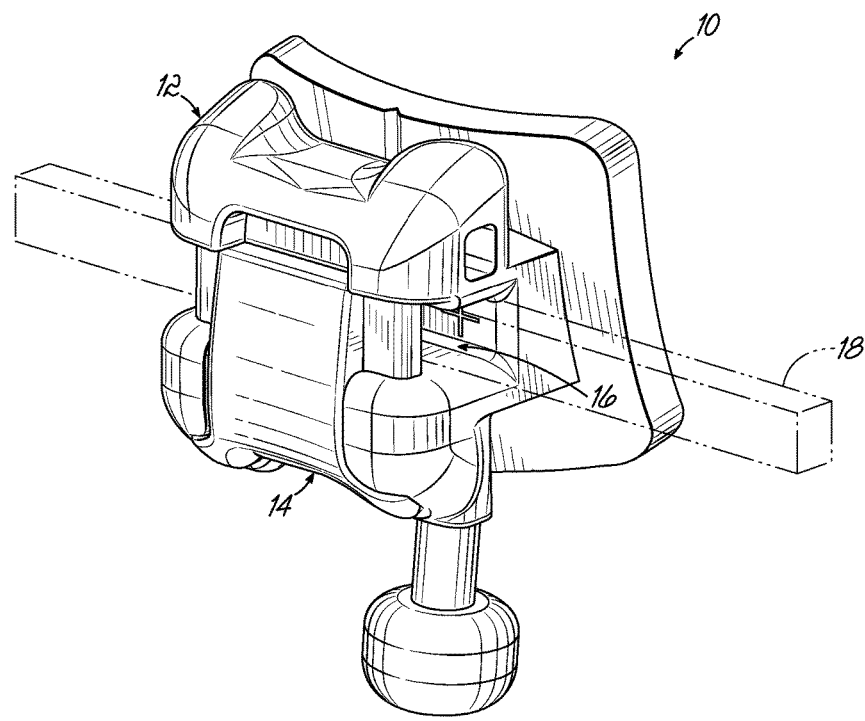
FIG. 2 is a perspective view of the orthodontic bracket of FIG. 1 with the movable member shown in the closed position.

To these and other ends, orthodontic appliances according to embodiments of the present invention, include, for example, self-ligating orthodontic brackets. With reference to FIGS. 1 and 2, in one embodiment, a self-ligating orthodontic bracket 10 includes a bracket body 12 and a movable member coupled to the bracket body 12. The exemplary self-ligating orthodontic bracket 10 shown in FIGS. 1 and 2 is fully disclosed in commonly owned U.S. Pat. No. 8,033,824, issued Oct. 11, 2011, and titled "Self-Ligating Orthodontic Bracket and Devices for Deploying Same," the disclosure of which is incorporated by reference herein in its entirety. The exemplary bracket disclosed in FIGS. 1 and 2 may further include a component of a Ferromagnetic Memory Shape Alloy (FSMA). While this component is not shown in FIG. 1 or 2, the remaining figures schematically depict an actuator and/or a movable member including an FSMA. The FIGS. 1 and 2 are provided for the purpose of providing a context for embodiments of the self-ligating orthodontic brackets illustrated in FIGS. 3-10. The figures, when are taken together and with the explanation below, fully explain the embodiments of the present invention. It will be appreciated that while passive self-ligating brackets are shown and described, embodiments of the present invention are not limited to passive self-ligating brackets. Specifically, embodiments of the present invention may be utilized in active ligation brackets as are known by those of ordinary skill in the art.

With reference to FIGS. 1 and 2, the movable member may include a ligating slide 14 coupled with the bracket body 12. The bracket body 12 includes an archwire slot 16 formed therein that is configured to receive an archwire 18 (shown in phantom line) for applying corrective forces to a tooth (not shown). The ligating slide 14 is movable between an opened position (FIG. 1) in which the archwire 18 is insertable into the archwire slot 16, and a closed position (FIG. 2) in which the archwire 18 is retained within the archwire slot 16. The ligating slide 14 may be movable with an actuator (not shown in FIGS. 1 and 2) including an FSMA, described below, instead of with a finger nail or dental tool. The actuator may be secured to one or both of the bracket body 12 and the ligating slide 14. The clinician may selectively magnetically activate the actuator.

The bracket body 12 and the ligating slide 14 collectively form a self-ligating orthodontic bracket for use in corrective orthodontic treatments. While the movable member may be described herein as a ligating slide, the invention is not as limited as the movable member may include other movable structures, for example, a latch, a spring clip, and a door that are capable of being moved between an opened position and a closed position as is set forth in detail below.

Figure 3:
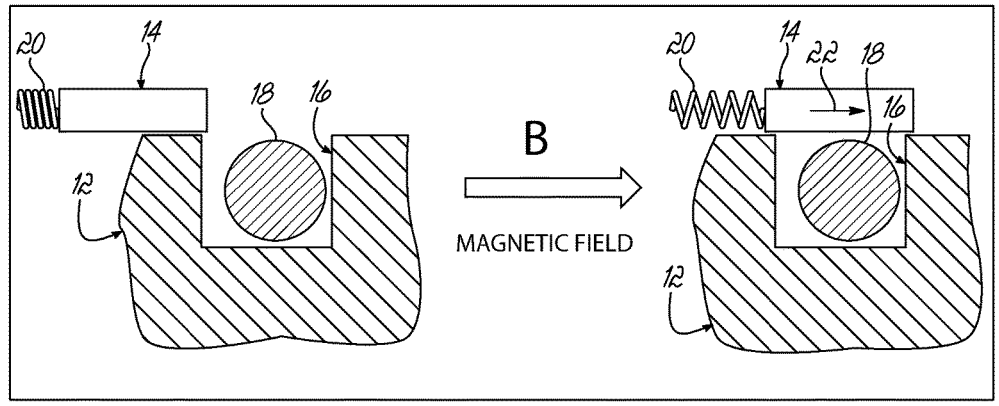
FIGS. 3-10 are cross-sectional view schematic representations of self-ligating orthodontic brackets according to embodiments of the invention in which manipulation of a movable member includes exposure of at least a portion of the orthodontic bracket to a magnetic field or magnetic field gradient.

In addition to the above and with reference to FIG. 3, in one embodiment, the orthodontic bracket 10 includes an actuator 20 coupled to each of the bracket body 12 and the ligating slide 14. The actuator 20 may alternatively be coupled only to the bracket body 12 or only to the ligating slide 14. By the term "actuator," it is meant a mechanism that is capable of moving relative to the bracket body 12 when activated by exposure to a magnetic field (B) or to a magnetic field gradient. The actuator 20 is configured to move relative to the bracket body 12. In the embodiment shown in FIG. 3, the actuator 20 also moves the movable member, for example, between the opened and closed positions. Movement of the movable member according to embodiments of the invention may be achieved in the absence of physical contact with any portion of the orthodontic bracket 10. Instead, manipulation of the movable member is achieved via exposure of the actuator 20 to a magnetic field (B).

It will be appreciated that a magnetic field (B) may be generated by a permanent magnet or an electromagnet (not shown) and is not visible to the human eye. The magnetic field nonetheless extends beyond the exterior surfaces of the magnet. A magnetic field gradient, as that term is used herein, refers to the rate of change of the magnetic field strength over distance. While the actuator may be described herein with regard to a magnetic field, it will be appreciated that embodiments of the invention are not limited to being useful only when exposed to a uniform magnetic field. In this sense, reference to magnetic field herein refers to both a magnetic field and a magnetic field gradient. As is known, objects that enter a magnetic field may interact with it. In this way, bringing a magnetic field into proximity of the actuator 20 may allow manipulation of the movable member though neither the actuator 20 nor the movable member may be physically contacted by the magnet, a tool, or by the clinician. In other words, the movable member can be manipulated in a non-contact manner during treatment.

Embodiments of the present invention thus include a non-contact bracket ligating system in which orthodontic treatment may be facilitated by a reduction in problems associated with the manipulation of self-ligating brackets. Specialized tools for moving the movable member may be dispensed with. A handheld device capable of generating a magnetic field may take the place of multiple customized tools. This may reduce problems associated with the treatment and may also reduce or eliminate patient discomfort during the exchange of archwires from the individual's teeth during treatment. Advantageously, patients need not be anxious or concerned that the clinician accidently poke or jab the patient in the lip or gum with a dental tool or finger nail during opening or closing of the movable member. Ultimately, embodiments of the system may also reduce chair time and facilitate more widespread adoption of orthodontic treatment.

In the exemplary embodiment shown in FIG. 3, the actuator 20 includes a coil spring-shaped member. When activated, the coil spring-shaped member provides a force that moves the ligating slide 14 relative to the bracket body 12. Manipulation of the actuator 20 may include moving the ligating slide 14 from the opened position to the closed position (as is indicated by arrow 22), moving the ligating slide 14 from the closed position to the opened position, or moving the ligating slide 14 in both directions, that is, from the opened position to the closed position and from the closed position to the opened position.

To that end, at least a portion of the actuator 20 is made of a ferromagnetic shape memory alloy (FSMA), such as, one or more alloys of the nickel-manganese-gallium (NiMnGa), nickel-manganese-aluminum (NiMnAl), or iron-palladium (FePd) systems. In one embodiment, the actuator 20 is completely formed of, that is, 100% FSMA. By way of example, and not limitation, one exemplary alloy of the FePd system includes about 70 at. % Fe and about 30 at. % Pd. Additional substitution of palladium (Pd) with cobalt (Co) and/or nickel (Ni) is favorable and may result in an increase in magnetization potential of the FSMA. One exemplary alloy is 70 at. % Fe, 25 at. % Pd, and 5 at. % Ni. Furthermore, copper (Cu) additions may also enhance magneto crystalline anisotropy, which may improve the mechanical work output of the actuator 20, and thus increase the capability of the actuator 20 to move larger, more complex movable members and/or to move the movable member over greater distances. It will be appreciated that FSMAs respond to a magnetic field (B) and that there are at least three mechanisms by which the actuator 20 including an FSMA may be activated.

According to one method, a magnetic field (B) may induce austenite phase transformation, effectively reducing the transformation temperature of the alloy. The magnetic field (B) may also induce internal magnetic forces in the alloy and, consequently, spontaneously drive stress-induced martensitic phase transformation. In other words, the magnetic field (B) may induce a crystal structure change from an FCC (Face Centered Cubic) to an FCT (Face Centered Tetragonal) structure. Embodiments of the present invention are not bound by any particular theory for their functionality. However, it is believed that according to one theory, the stable phase has an austenitic structure that, when exposed to a magnetic field (B), causes phase transformation to a stress-induced martensitic phase. Deformation of the stress-induced martensitic phase may proceed according to known stress-strain hysteresis curves. According to another theory, the magnetic field (B) may induce martensite variant rearrangement. At least one variant accommodates strain to a greater degree than one or more other variants. And, according to a third theory, a magnetic field gradient induces a magnetic force internal to the FSMA, which causes stress-induced martensitic phase transformation from austenite. The magnetic field gradient may then cause displacement of the FSMA or a portion thereof. The transformation is reversible and very fast, for example, from about 0.01 second to about 1 second. According to embodiments of the invention, the magnetic field strength is sufficient to activate the actuator 20, according to any single one of the above-identified theories and, for example, the magnetic field strength may be on the order of from about 0.1 Tesla to about 1 Tesla.

A bulk polycrystalline FSMA may be made from nanoparticles of the alloy fused together by spark plasma sintering. The nanoparticles prior to sintering may be sized to produce a sintered alloy having an average grain size of less than about 50 nm. It will be appreciated, however, that embodiments of the invention are not limited to this range. The sintered alloy may contain an average grain size greater than 50 nm, for example, the average grain size may range up to about 50 μm or larger. Actuators, as described herein, may be formed (e.g., machined or forged) from the bulk FSMA or may be formed by sintering the nanoparticles in the configuration of an actuator or in the configuration of an orthodontic component, such as, by a near net-shape forming process.

In one embodiment, and with reference to FIG. 3, exposure of the actuator 20 (in the configuration of a coil spring-shaped member) to a magnetic field (B) or magnetic field gradient causes extension of the actuator 20 and, consequently, movement of the ligating slide 14 from the opened position toward the closed position. Relative movement may be by translational movement of the ligating slide 14. For example, the ligating slide 14 is shown in the opened position on the left side of FIG. 3 and in the closed position on the right side of FIG. 3 with the actuator 20 shown extended under the influence of the magnetic field (B), as is indicated by arrow 22. The bracket body 12 may guide the sliding motion or translation of the ligating slide 14 toward the closed position. Rotational/pivotal motion of the movable member as a result of activation of the actuator 20 is also possible according to similar principles and is as described below.

With continued reference to FIG. 3, the FMSA of the actuator 20 may normally be in an austenitic phase in the absence of a magnetic field (B), such as on the right-hand side of FIG. 3. Upon application of the magnetic field (B), the martensite may transform to austenite. Under the internal magnetic stress, the austenitic phase may transform at least in part to stress-induced martensite. The stress-induced martensitic transformation may then permit extension of the actuator 20 (and movement of the ligating slide 14) under the applied magnetic force with little or no additional external force on the ligating slide 14. For example, the actuator 20 may extend upon exposure to the magnetic field (B) and in the absence of any other manually applied force on the actuator 20 or on the ligating slide 14.

Upon removal of the magnetic field (B), the FSMA of the actuator 20 may revert in whole or in part to the martensitic phase or to the austenitic phase. In this regard, the actuator 20 may contract when the magnetic field (B) is removed and therefore revert to a configuration similar to or the same as that shown on the left side of FIG. 3, in which the ligating slide 14 is shown in the opened position.

In practice, the clinician may bring a device (not shown) capable of generating a magnetic field (B) into proximity, though not necessarily into direct contact, with the actuator 20. The clinician may then selectively expose the actuator 20 to a magnetic field. By way of example, and not limitation, the device may be a handheld device, such as a permanent magnet or a battery-powered electro magnet capable of providing the necessary magnetic field. Thus, selective exposure may include bringing a permanent magnet into close proximity to the actuator 20 to expose the actuator 20 to the magnetic field (B) or selectively energizing an electromagnet proximate to the actuator 20.

As described generally above, once the actuator 20 is sufficiently exposed to the magnetic field (B), it may extend and thereby move the ligating slide 14 from the opened position to the closed position. It will be appreciated that exposure of the actuator 20 to the magnetic field (B) does not require contact between the device and the actuator 20 (or any portion of the orthodontic bracket 10), because the magnetic field (B) extends beyond the device to envelope the actuator 20. The clinician may therefore selectively operate the ligating slide 14 by positioning the device proximate to the orthodontic bracket 10 without contacting any portion of the orthodontic bracket 10. According to embodiments of the present invention, the clinician may not need to contact the orthodontic bracket 10 with any tool during treatment. And, because the magnetic field (B) encompasses a relatively large volume beyond the magnet, manipulation of the ligating slide 14 may not require precise placement or insertion of a tool into direct contact with a specifically targeted portion of the bracket. Advantageously, treatment problems associated with a lack of or limited visual acuity and/or lack of or limited manual dexterity of the clinician may be reduced or completely eliminated.

Figure 4:
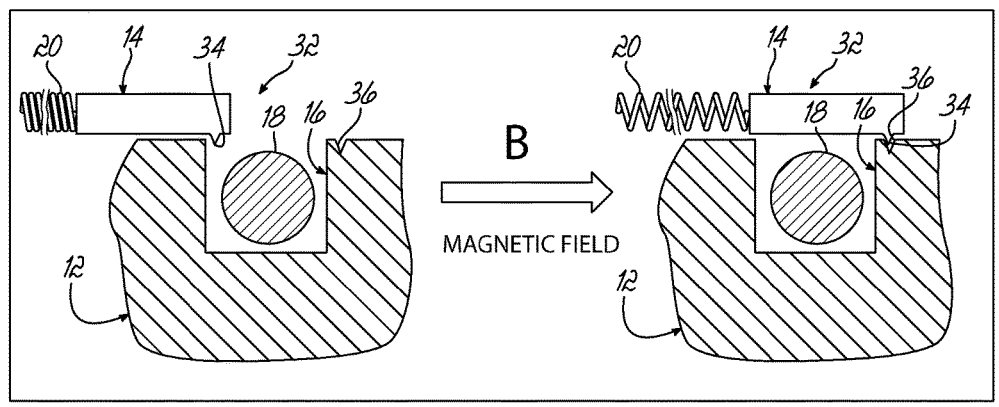

Referring now to FIG. 4, in which like reference numerals refer to like features of FIG. 3, in one embodiment, the orthodontic bracket 10 includes a locking mechanism 32 that is configured to hold the ligating slide 14 in the closed position. In the exemplary locking mechanism 32, the ligating slide 14 includes a projection 34 and the bracket body 12 includes a recess 36. In this embodiment, when the actuator 20 is exposed to a magnetic field (B), the actuator 20 extends and so moves the ligating slide 14 from the opened position to the closed position. In the closed position, the projection 34 is positioned within the recess 36, as is shown in the right-hand side of FIG. 4. The interference between the projection 34 and the bracket body 12 defining the recess 36 holds the ligating slide 14 in the closed position, and upon removal of the magnetic field, the ligating slide 14 remains in the closed position. The locking mechanism 32 may therefore retain the ligating slide 14 in the closed position during orthodontic treatment.

In this regard, removal of the magnetic field (B) may allow the stress induced martensite to transform back to austenite. In embodiments in which the actuator 20 is secured to both the bracket body 12 and the ligating slide 14, the actuator 20 may bias the ligating slide 14 toward the opened position. The locking mechanism 32, however, retains the ligating slide 14 in the closed position. The locking mechanism 32 restricts movement of the ligating slide 14 so as to retain the actuator 20 in an extended or expanded configuration. Because the locking mechanism 32 may hold the actuator 20 in an expanded state, the actuator 20 may become biased toward the closed position when the magnetic field (B) is removed from the actuator 20. In this embodiment, the clinician may disengage the locking mechanism 32 in which case the biasing force produced by the actuator 20 being in an extended position spontaneously retracts the ligating slide 14 to the opened position.

It will be appreciated that to open the ligating slide 14 once it is in the closed position, the clinician may use a scalar or another common dental tool to disengage the locking mechanism 32. Once unlocked, any bias in the actuator 20 may automatically retract the ligating slide 14 toward the opened position. Alternatively, in embodiments in which the actuator 20 does not significantly bias the ligating slide 14, the clinician may use a tool or a finger to disengage the locking mechanism 32 and push the ligating slide 14 to the opened position.

Embodiments of the present invention are not limited to those in which the actuator 20 is biased toward the opened position when the ligating slide 14 is locked in the closed position. In one embodiment, the actuator 20 is not attached or, in other words, secured to each of the bracket body 12 and the ligating slide 14. In such a configuration, exposure of the actuator 20 to a magnetic field gradient may be sufficient to move the ligating slide 14 to the closed position as the actuator 20 extends. Once the ligating slide 14 is in the closed position and the magnetic field (B) or magnetic field gradient is removed, the actuator 20 may spontaneously revert to a contracted configuration. Because the actuator 20 is not attached to each of the ligating slide 14 and the bracket body 12, it is not stretched between the bracket body 12 and the ligating slide 14. Thus, in the absence of being secured to each of the ligating slide 14 and the bracket body 12, reversion of the actuator 20 to the contracted configuration may not further move or bias the movement of the ligating slide 14 from the closed position. The locking mechanism 32 still maintains the ligating slide 14 in the closed position by resisting normal forces encountered during use of the orthodontic bracket 10.

Figure 5:
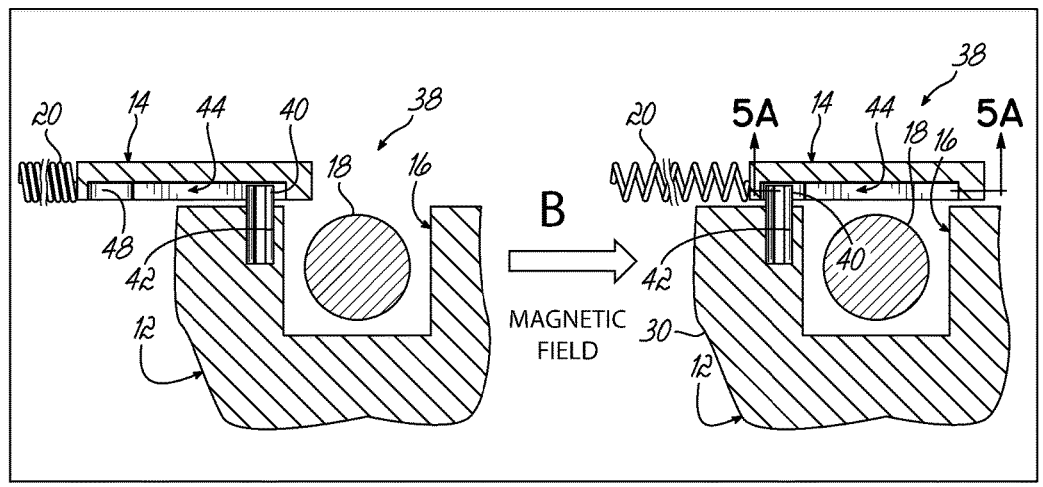

With reference now to FIG. 5, a locking mechanism 38 is shown. In this embodiment, the ligating slide 14 includes a generally elongated cylindrical, tubular spring pin 40 coupled to the bracket body 12 in a bore 42 and a retaining slot 44 formed in the ligating slide 14. The operation of the spring pin 40 in cooperation with the retaining slot 44 is more fully described in the '824 Patent that is incorporated by reference herein, as set out above. Although this embodiment is described with the spring pin 40 associated with the bracket body 12 and the retaining slot 44 associated with the ligating slide 14, those of ordinary skill in the art will recognize that the invention is not so limited. For example, although not shown, the spring pin 40 may be coupled to the ligating slide 14 and the retaining slot 44 may be formed in the bracket body 12.

Figure 5A:
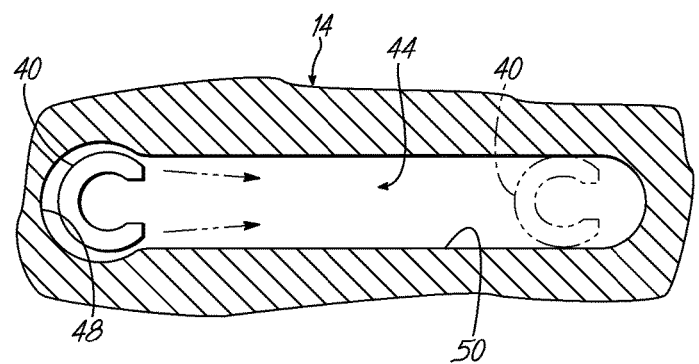

When the ligating slide 14 is coupled to the bracket body 12, the spring pin 40 is received in retaining slot 44. In one aspect of the invention, the spring pin/retaining slot locking mechanism 38 provides for securing the ligating slide 14 in at least the closed position. Unlike the locking mechanism 32, shown in FIG. 4, the locking mechanism 38 may be located on the same side of the bracket body 12 as the actuator 20. That is, the locking mechanism 38 and the actuator 20 are located on the same side of the archwire slot 16. To lock the ligating slide 14 in the closed position, the spring pin 40 is capable of radially expanding and contracting depending on the force being imposed thereon. The retaining slot 44 is configured to cooperate with the radial expansion and contraction of the spring pin 40 so as to lock the ligating slide 14 in the closed position. In this regard, the retaining slot 44 includes an enlarged portion 48 and a straight portion 50, shown best in FIG. 5A.

In operation, the clinician exposes the actuator 20 to a magnetic field (B) or magnetic field gradient that causes the actuator 20 to extend and thus push the ligating slide 14 from the opened position to the closed position. This is shown schematically from the left side to the right side of FIG. 5, respectively. During movement of the ligating slide 14, the spring pin 40 slides in cooperation with the retaining slot 44, particularly the straight portion 50. When the ligating slide 14 reaches the closed position, the spring pin 40 expands into the enlarged portion 48 of the retaining slot 44. The spring pin 40 is shown in its expanded configuration in the enlarged portion 48 in FIG. 5A. At this location, the spring pin 40 and the ligating slide 14 form an interference fit so as to resist movement of the ligating slide 14 toward the opened position. The spring pin 40 is shown in its contracted configuration (in phantom line) in the straight portion 50 in FIG. 5A.

Figure 6:
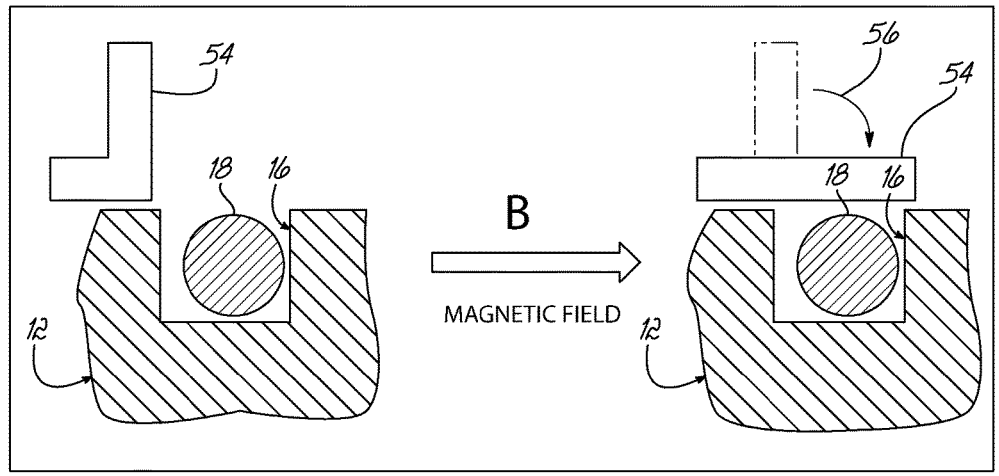

In one embodiment, and with reference to FIG. 6, in which like reference numerals refer to like features of FIG. 3, the movable member may include or incorporate an actuator. In one embodiment, the actuator is the movable member. In other words, the actuator forms nearly the entire or 100% of the movable member. For example, as shown in FIG. 6, an actuator 54 is shown as a door-like movable member having both opened and closed configurations resulting from a change in shape due to exposure to a magnetic field.

In this embodiment, it will be appreciated that rather than having two components (e.g., an actuator separate from a movable member) responsible for closing the archwire slot 16, a single movable member is operable to close off the archwire slot 16. In the opened position, shown on the left-hand side of FIG. 6, the actuator 54 has an L-shaped configuration when in the opened position. And, when exposed to a magnetic field (B), the actuator 54 changes shape to a planar-like configuration in which a portion of the actuator 54 extends across and thus closes the archwire slot 16 and retains the archwire 18 within the archwire slot 16. In this regard, at least a portion of the actuator 54 is moved and/or changes shape under the influence of a magnetic field (B) or magnetic field gradient as indicated by the arrow 56 on the right-hand side of FIG. 6, in which the actuator 54 is shown in the opened configuration (in phantom line) and in the closed position. Movement may be effectuated by a portion of the microstructure transforming from an austenitic phase to a stress-induced martensitic phase when exposed to the magnetic field (B). The shape change may appear as a rotational-like movement of a portion of the actuator 54 as is schematically shown by arrow 56.

Though not shown, it will be appreciated that the reverse process to that described in the preceding paragraph may also be utilized. Specifically, while the actuator 54 is shown and described as moving from the opened position to the closed position when exposed to the magnetic field (B), it is also possible to cause the actuator 54 to move from the closed position, shown in the right-hand side of FIG. 6, to the opened position, shown in the left-hand side of FIG. 6, when exposed to the magnetic field (B). In either case, whether the actuator 54 is openable and/or closable on exposure to the magnetic field (B) may depend upon the normal shape of the actuator 54 when it is in an austenitic state. That is, the actuator 54 may have a normally opened configuration or a normally closed configuration.

Figure 7:
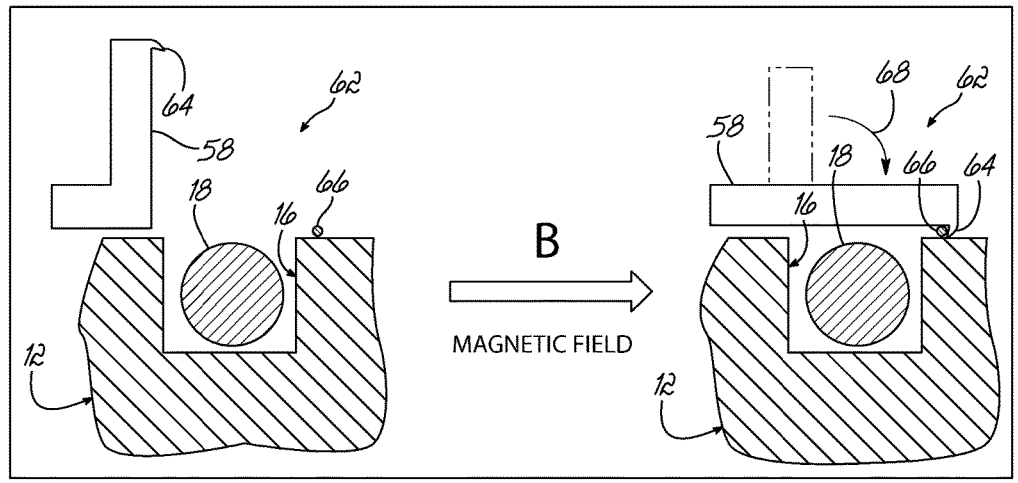

With reference to FIG. 7, in which like reference numerals refer to like features of FIG. 6, another door-like movable member is shown. As set forth above with reference to FIG. 6, the door-like movable member may include or be formed entirely of an actuator 58. In the embodiment shown, actuator 58 is the door-like movable member. Similar to the embodiment of FIG. 6, the actuator 58 closes the archwire slot 16 when exposed to the magnetic field (B). The orthodontic bracket 10 further includes a locking mechanism 62 to lock the movable member in the closed position. To that end, the locking mechanism 62 includes a projection 64 extending from the movable member and a dimple 66 in the bracket body 12. It will be appreciated, however, that the projection 64 may extend from the bracket body 12 and the dimple 66 may be defined by the actuator 58.

In operation, and with continued reference to FIG. 7, the clinician may insert the archwire 18 into the archwire slot 16 when the actuator 58 has an L-shaped configuration (i.e., the movable member is in the opened position), as is shown in the left-hand side of FIG. 7. To close the movable member, the clinician exposes at least the actuator 58 to a magnetic field (B) or magnetic field gradient. Under the forces imposed by the magnetic field (B), which may be internal to the actuator 58, the actuator 58 changes shape from the L-shaped configuration to a planar-like configuration, shown in the right-hand side of FIG. 7. The shape change may be accompanied by movement of the actuator 58 across the archwire slot 16 as is indicated generally by arrow 68 on the right-hand side of FIG. 7. The shape change of the actuator 58 may also provide sufficient force to engage the locking mechanism 62. In this regard, the projection 64 contacts the indentation 66. The engagement of the locking mechanism 62 may be sufficient to hold the archwire 18 within the archwire slot 16 during orthodontic treatment.

In addition, the locking mechanism 62 may resist any bias of the actuator 58 towards the opened position, that is, the locking mechanism 62 may resist a change in shape to the L-shaped configuration upon removal of the magnetic field (B). It will be appreciated that to open the movable member, the clinician may use a dental tool (shown in FIGS. 11 and 11A and described below) to unlatch or otherwise disengage the locking mechanism 62. In the event that the actuator 58 is biased toward the L-shaped configuration, unlatching the locking mechanism 62 with a tool may release the actuator 58 so that it spontaneously changes shape toward the L-shaped configuration. In other words, the actuator 58 may have a normally opened configuration to which it will spontaneously move in the absence of a magnetic field and in the absence of engagement of the locking mechanism 62. It will be appreciated that while the actuator 58 is described as having a normally opened configuration in the absence of the magnetic field (B), embodiments of the present invention are not limited to actuators having a normally opened configuration.

Specifically, embodiments of the present invention may include actuators that have a normally closed configuration. In these embodiments, exposure of the actuator to the magnetic field (B) may cause the actuator to change shape to a configuration that opens the archwire slot 16 so as to provide access to the archwire slot 16. Upon removal of the magnetic field (B), the actuator may then spontaneously change shape to its normally closed configuration to effectuate orthodontic treatment. In such embodiments, a locking mechanism may not be included because the normally closed configuration of the movable member may be sufficient to resist forces imposed by the archwire 16 on the movable member during treatment.

Figure 8:
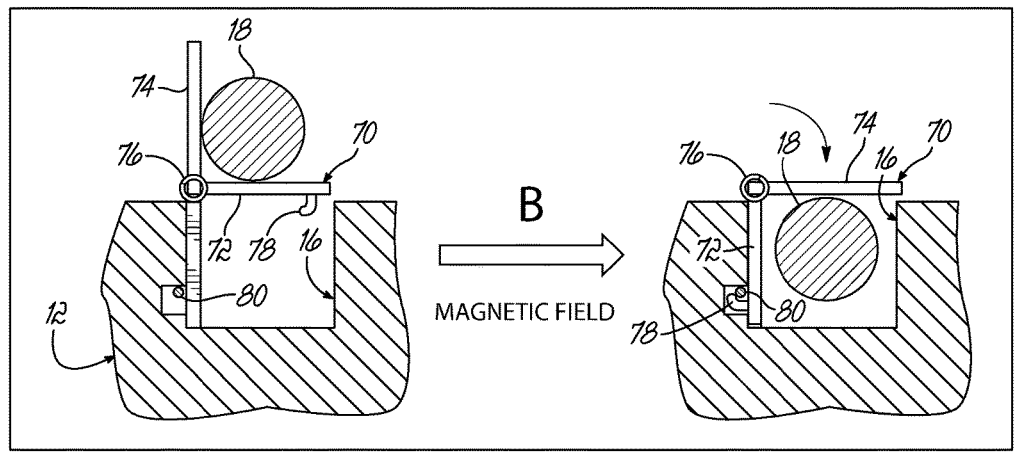

In one embodiment, and with reference to FIG. 8, in which like reference numerals refer to like features of the figures, the orthodontic bracket 10 includes a movable member in the configuration of a double door-like member 70 having a generally L-shaped cross-sectional configuration. The double door-like member 70 may be pivotal or rotate relative to the bracket body 12 between an opened position (shown in the left-hand side of FIG. 8) and a closed position (shown in the right-hand side of FIG. 8). In this regard, the double door-like member 70 may include a first leg 72 and a second leg 74 extending transversely relative to the first leg 72 and may be configured to receive the archwire 18 between the first leg 72 and the second leg 74. For example, in one embodiment, the first leg 72 may extend from the second leg 74 at approximately 90° so that the archwire 18 may be positioned between the first leg 72 and the second leg 74 directly above the archwire slot 16. While the first leg 72 and the second leg 74 may be approximately the same length, embodiments of the present invention are not limited to each of the legs 72, 74 having the same length. For example, in one embodiment, the second leg 74 may be longer such that, in the closed position, the second leg 74 abuts a portion of exterior surface of the bracket body 12 when the double door-like member 70 is rotated to the closed position. In one embodiment, the first leg 72 includes a projection 78, such as a hook shaped member. The projection 78 cooperates with the bracket body 12, as is described below, to secure the double door-like member 70 in a closed position.

As shown, the double door-like member 70 may be pivotally attached to the bracket body 12 at one edge of the archwire slot 16 by an actuator 76. Pivotal attachment allows the clinician to rotate the double door-like member 70 with archwire 18 therein about an axis that is substantially parallel to the archwire slot 16 into the closed position.

Similar to other embodiments of the actuator described herein, at least a portion of the actuator 76 may be made of an FSMA. In the embodiment shown, the actuator 76 may have a clock or torsion spring-type configuration sufficient to provide rotation of the double door-like member 70 when the actuator 76 is activated. The actuator 76 may be a separate component attached to each of the double door-like member 70 and the bracket body 12 proximate the archwire slot 16. The actuator 76 may be the sole means for attachment between the double door-like member 70 and the bracket body 12 or may be used in cooperation with a hinge-like member (not shown) that defines an axis of rotation of the actuator 76 relative to the bracket body 12. It will be appreciated that embodiments of the present invention are not limited to connection of the double door-like member 70 to the bracket body 12 via the actuator 76 or another hinge-like member with an actuator being coupled to both the door member 70 and the bracket body 12.

With continued reference to FIG. 8, the bracket body 12 further includes a recess 80 in which there is located a projection 82, such as, a dimple or pin. The recess 80 is configured to receive the projection 78 when the double door-like member 70 is in the closed position. Furthermore, the projection 78 may cooperate with the projection 82 in the recess 80 to secure the double door-like member 70 in the closed position to effectuate orthodontic treatment.

Accordingly, during orthodontic treatment, when the double door-like member 70 is in the opened position, the first leg 72 extends only a portion of the distance across the archwire slot 16 with the second leg 74 extending outwardly from the bracket body 12. The clinician may insert the archwire 18 between the first leg 72 and the second leg 74, as is shown in the left-hand side of FIG. 8. Once the archwire 18 is so positioned, the actuator 76 may be exposed to a magnetic field (B) or magnetic field gradient. Similar to the coil spring-shaped actuator 20, described above in FIGS. 3 and 4, the magnetic field (B) may provide a magnetic force sufficient to transform at least some of the austenitic phase of the FSMA in the actuator 76 to martensite. The magnetic force may also be sufficient to cause extension of the actuator 76 and thus rotation of the actuator 76 and the double door-like member 70 relative to the bracket body 12. Rotation of the double door-like member 70 may be about an axis defined by the actuator 76 or about an axis defined by another hinge-like member (not shown).

By this rotational motion, the first leg 72 rotates into and through the archwire slot 16. In the embodiment shown, the first leg 72 forms a portion of one of the surfaces of the archwire slot 16 when the double door-like member 70 is in the closed position, as is shown in the right-hand side of FIG. 8. And, the second leg 74 rotates to a position relative to the first leg 72 in which the second leg 74 prevents the archwire 18 from escaping from the archwire slot 16. The second leg 74 may form an outermost boundary, for example, the labial-most side of the archwire slot 16, so as to passively ligate the archwire 18.

In one embodiment, the actuator 76 is configured such that the double door-like member 70 has a normally opened position shown in the left-hand side of FIG. 8. Accordingly, the double door-like member 70 may be secured in the closed position to prevent spontaneous movement of the double door-like member 70 toward the opened position. In this regard, securing the double door-like member 70 in the closed position via a locking mechanism (described above) may be sufficient to resist any bias associated with a change in shape of the actuator 76 that would, in the absence of being secured in the closed position, cause the double door-like member 70 to open. In other words, absent a mechanism to secure the double door-like member 70 in the closed position, the double door-like member 70 may spontaneously rotate toward the opened position once the magnetic field (B) is removed.

When secured in the closed position, to open the double door-like member 70, a tool (not shown) may be used to pull outwardly on the second leg 74 to forcibly unlatch the projection 78 from the projection 82. It will be appreciated that while embodiments of the invention shown in FIG. 8 are described as having a normally opened configuration in which the double door-like member 70 is positioned to receive an archwire therein (shown on the left-hand side of FIG. 8), embodiments of the invention are not limited to those with normally opened configurations. The orthodontic bracket 10 of FIG. 8 may include a double door-like member 70 having a normally closed position (shown on the right-hand side of FIG. 8). Such embodiments may require exposure of the actuator 76 to a magnetic field (B) to cause the door 70 to rotate toward the opened position.

Figure 9:
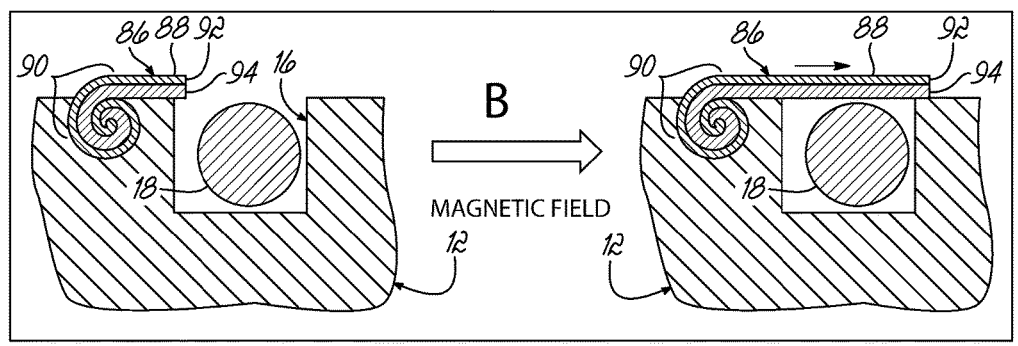

In one embodiment and with reference now to FIG. 9, in which like reference numerals refer to like features of FIG. 8, the movable member may be in the configuration of a coiled door member 86 having an opened position (shown in the left-hand side of FIG. 9) and a closed position (shown in the right-hand side of FIG. 9). The coiled door member 86 may include a planar portion 88 and a coiled portion 90. During use, described below, the coiled door member 86 uncoils so that the planar portion 88 is enlarged or lengthened so as to extend across the archwire slot 16 while the coiled portion 90 is simultaneously reduced in dimension.

As shown, the coiled door member 86 may be a layered member having at least two layers of different materials. By way of example only, and not limitation, the coiled door member 86 may include a layer 92 and at least one other layer 94 of a different material. The layer 92 may include an actuator of an FSMA. In one embodiment, the layer 92 is an actuator that is fully formed of FSMA. While the coiled door member 86 is shown as having a layer of the FSMA 92 forming an external surface of the coiled door member 86, it will be appreciated that the layer 92 and the layer 94 may be reversed so that the layer 94 forms an external surface on the coiled door member 86. Other, optional additional layers may be included in the coiled door member 86.

In one embodiment, the layer 94 is a metal, such as, a superelastic metal and, more particularly, a shape memory alloy (SMA) that is a non-ferromagnetic. By way of example only, the superelastic metal may be a nickel-titanium (NiTi), a copper-aluminum-manganese (CuAlMn) alloy, or a copper-aluminum-nickel (CuAlNi) alloy, among others.

In one embodiment, the coiled door member 86 is a two-layer composite material of, for example, a layer 92 of FSMA in direct contact with a layer 94 of SMA. The combination of the at least two layers 92, 94 may be used to determine whether the coiled door member 86 is closed or is opened when exposed to a magnetic field (B). By way of example only, and not limitation, the SMA of the layer 94 may have a normally closed or extended configuration, as is shown in the right-hand side of FIG. 9. That is, in the absence of the FSMA layer 92, at the temperature normally encountered in the human mouth, the layer 94 may be normally in the extended configuration with the planar portion 88 extending across the archwire slot 16. However, that normal configuration of the layer 94 may be resisted by the layer 92. That is, the layer 92 may have a normally open or retracted configuration, as is shown in the left-hand side of FIG. 9. That is, in the absence of the layer 94, at the temperature normally encountered in the human mouth, the layer 92 may be in the opened position. When combined, the two layers 92, 94 may compete with one another to maintain the coiled door member 86 in the opened position or in the closed position.

In this regard, in one embodiment in which the layer 92 is an FSMA and the layer 94 is an SMA, and with reference to the left-hand side of FIG. 9, the member 86 may have a normally opened configuration. Exposing the coiled door member 86 to a magnetic field (B) may facilitate extension of the planar portion 88 across the archwire slot 16, as is shown in the right-hand side of FIG. 9. Microstructurally, when exposed to the magnetic field (B), the FSMA layer 92 may at least partially transform from austenite to martensite. The martensite having a much lower modulus of elasticity than the modulus of elasticity of austenite. In one embodiment, the FSMA layer 92 completely transforms from austenite to martensite. Once the FSMA layer 92 is at least partially transformed, the layer 94 exhibits a modulus of elasticity greater than the modulus of elasticity of layer 92, which will then express its superelastic properties and retain its "remembered shape" by spontaneously extending the combined planar member 88 to the closed position shown on the right-hand side of FIG. 9.

Removing the magnetic field (B) allows martensite to transform back to austenite in the FSMA of layer 92. Consequently, in the austenitic state, the layer 92 may apply a stress to and forcibly deform the layer 94. This may cause the coiled door member 86 to retract to the opened position. Closing the coiled door member 86 is achieved by exposing at least the layer 92 to a magnetic field (B) or magnetic field gradient. The process of opening and closing the coiled door member 86 is reversible and much faster than manual operation of a movable member with a tool. The level of force required to open and/or close the coiled door member 86 may be designed by adjusting the relative proportions (e.g., thicknesses) of the two layers 92, 94 relative to one another or adjusting the characteristic transformation temperature of the SMA of the layer 94.

Further, it will be appreciated that the reverse configuration for the coiled door member 86 is also possible. That is, the layer 92 may have a normally closed or extended configuration and the layer 94 may have a normally open or retracted configuration. In this embodiment, the coiled door member 86 may have a normally closed position and exposing the layer 92 to a magnetic field (B) may cause the coiled door member 86 to retract to open the archwire slot 16.

Figure 10:
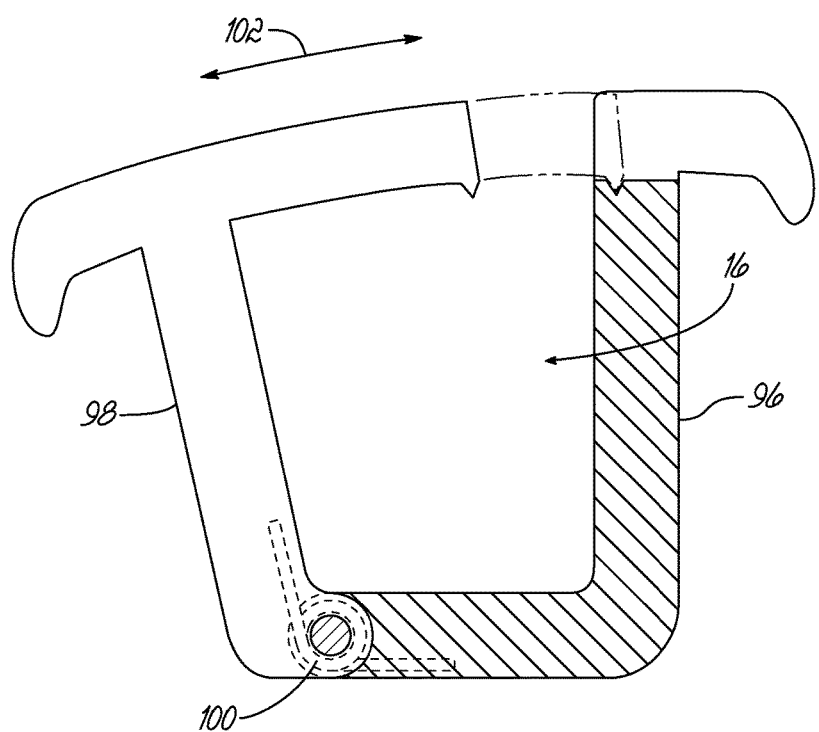

With reference now to FIG. 10, in which like reference numerals refer to like features throughout the figures, in one embodiment of the invention, the orthodontic bracket 10 includes a bracket body 96 (shown in partial cross-section). A movable member in the form of a latch 98 is pivotally connected to the bracket body 96. An actuator 100 operates on one or both of the latch 98 and the bracket body 96 to cause relative motion between the two when exposed to a magnetic field (B). In cross-section, the bracket body 96 and latch 98 have a Venus fly trap-like or clam-like configuration, as shown.

In general, the actuator 100 is proximate an axis about which the latch 98 may move relative to the bracket body 96 as indicated by the arrow 102. In the embodiment shown, in contrast to the embodiment shown in previous figures, the actuator 100 is remote from the exterior surface of the bracket body 96. The latch 98 has opened and closed positions in which an archwire (not shown) may be inserted into and removed from the archwire slot 16, respectively.

As with previous embodiments, the latch 98 may have a normally opened or a normally closed position. That is, in the absence of a magnetic field (B), the latch 98 may be normally closed, or in the absence of a magnetic field, the latch 98 may be normally open. It will be appreciated that in the normally closed position, the orthodontic bracket 10 may resist inadvertent opening due to any propensity of the patient to abuse the orthodontic bracket 10. As shown schematically, the actuator 100 may have a configuration of a coil spring though the configuration is not limited thereto.

During use, exposing the actuator 100 to a magnetic field (B) may simultaneously transform austenite into martensite while simultaneously rotating the latch 98 under the influence of the magnetic field. Similar to previous embodiments, no contact may be required to operate the latch 98 to either open the latch 98 and/or close the latch 98.

Figure 11:
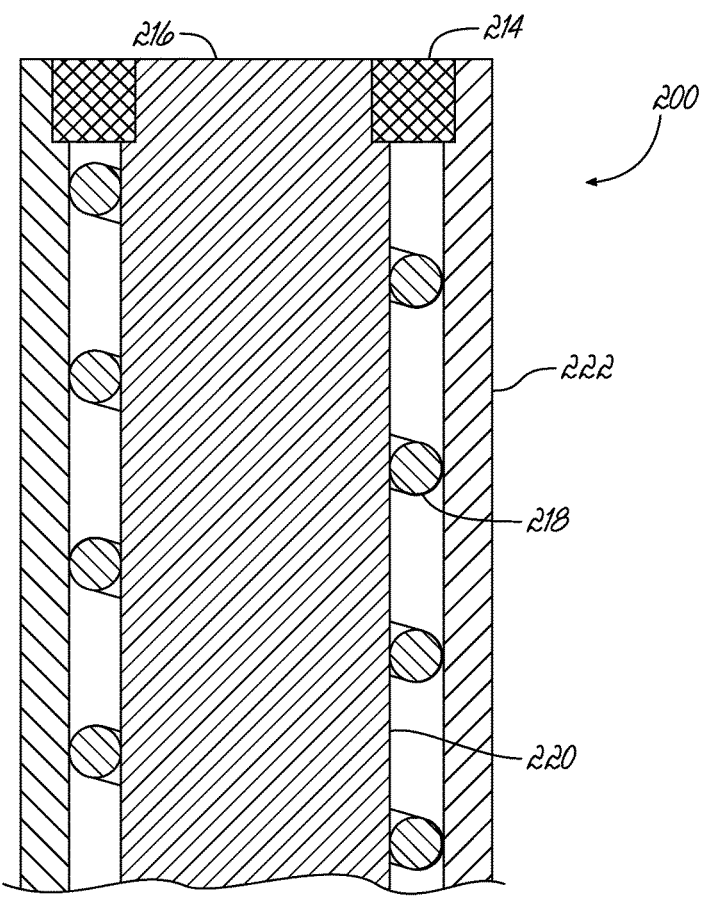
FIG. 11 is a cross-sectional view of a tool configured to produce a magnetic field or magnetic field gradient.
Figure 11A:
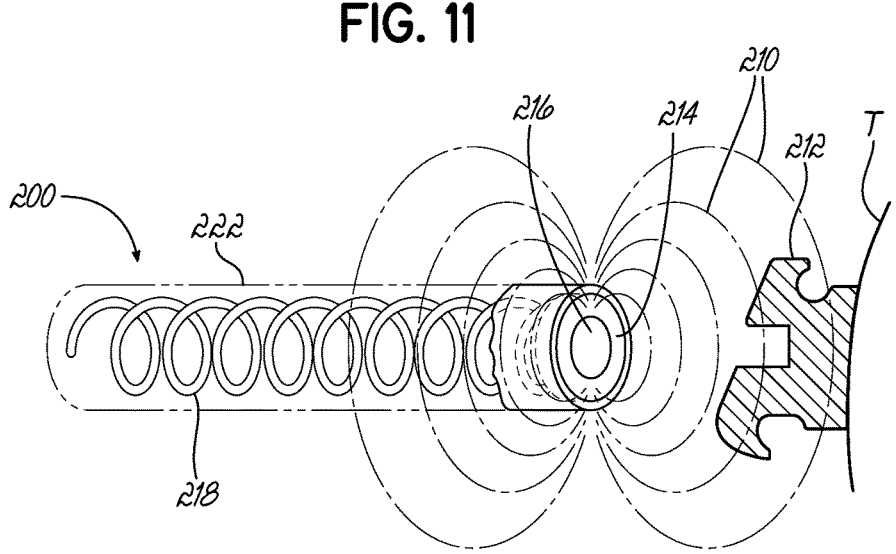
FIG. 11A is a schematic of the tool of FIG. 11 shown positioned relative to an orthodontic bracket on the surface of a tooth with a magnetic field emanating from the tool and exposing the orthodontic bracket to the magnetic field according to one embodiment of the invention.

As summarized above, in one embodiment and with reference to FIGS. 11 and 11A, the clinician uses a dental tool 200 configured to generate a magnetic field (B) or magnetic field gradient 210 proximate an orthodontic bracket 212 having an FSMA actuator according to one embodiment of the invention described herein. The dental tool 200 may be hand held and may be selectively activated to produce the magnetic field gradient 210 or may continuously produce the magnetic field gradient 210. As shown in FIG. 11, the dental tool may include a permanent magnet 214 the end 216 of which is configured to be positioned proximate the orthodontic bracket 212 on the tooth T (FIG. 11A). The dental tool 200 may further include a coil 218 and a yoke or core 220 of a ferromagnetic metal, such as, iron, iron silicide, or certain magnetic stainless steels. A housing 222 may surround the coil 218, the core 220, and the permanent magnet 214. The dental tool 200 may produce the magnetic field gradient 210 by selective electrical activation of the coil 218 and the core 220.

In use, the clinician may bring the tool 200 proximate an orthodontic bracket 212 that includes an FSMA actuator (not shown). Once the tool 200 is properly positioned, the clinician may selectively activate the tool 200 by pressing or switching an on-off switch such that the magnetic field gradient 210 is produced. As described above, exposing the orthodontic bracket 212 to a magnetic field gradient 210 may selectively activate the FSMA actuator and result in movement of at least one component of the orthodontic bracket 212, as is described in conjunction with the embodiments above.

The following paragraphs further describe some of the embodiments of the present invention that are conceptually shown and described above with reference to FIGS. 3-6. While the following embodiments are not described in conjunction with a latch or other means for securing the movable member in the closed position, it will be appreciated that a latch or any of the other securing mechanisms described above may be incorporated into any of the following embodiments to secure the movable member in the closed position. In particular, these securing mechanisms may be incorporated when an FSMA actuator maintains the movable member in a normally opened configuration in which when the FSMA actuator is exposed to a magnetic field (B) or a magnetic field gradient, the FSMA actuator closes the movable member.

With reference to FIGS. 12-15, in one embodiment, a self-ligating orthodontic bracket 310 includes a bracket body 312 and a movable member, such as, a ligating slide 314, coupled to the bracket body 312. The bracket body 312 includes an archwire slot 316 formed therein that is configured to receive an archwire (not shown) for applying corrective forces to a tooth (not shown). The bracket body 312 includes an aperture 315 in a sidewall of the bracket body 312 positioned in a lingual-labial direction above the archwire slot 316. The bracket body 312 may include a recess 336 opposing the aperture 315 across the archwire slot 316. As shown, the ligating slide 314 may be slidable through the aperture 315 and received in the recess 336. The ligating slide 314 may be coupled to the bracket body 312 by an FSMA actuator 320.

In the exemplary embodiment shown in FIGS. 12-15, the FSMA actuator 320 is in the form of a flat spring-shaped member that may couple the ligating slide 314 to the bracket body 312. The actuator 320 may be contiguous with the ligating slide 314 and may be welded or otherwise metallurgically connected to the ligating slide 314 at one end thereof. In the embodiment shown, the actuator 320 may form a lingual leg of the ligating slide 314. A pin 322 may secure the FSMA actuator 320 at the other end thereof to the bracket body 312. The pin 322 may be secured in a bore (not shown) by staking, laser welding, or other means known in the art.

According to embodiments of the present invention, the actuator 320 may have a normally opened configuration or a normally closed configuration similar to actuators described above. If the FSMA actuator 320 has a normal configuration in the absence of a magnetic field (B) or a magnetic field gradient in which the ligating slide 314 is closed (i.e., a normally closed configuration), the ligating slide 314 may be opened by exposing the FSMA actuator 320 to a magnetic field (B). If the FSMA actuator 320 has a normal configuration in which the ligating slide 314 is opened, the ligating slide 314 may be closed by exposing the FSMA actuator 320 to a magnetic field (B).

In either of these normal configurations, the ligating slide 314 is movable between an opened position (FIG. 14) and a closed position (FIG. 12) in which the archwire is retained within the archwire slot 316. The ligating slide 314 may be movable with the FSMA actuator 320 coupled to each of the bracket body 312 and the ligating slide 314, similar to the embodiments described above. As shown best in FIG. 13, the flat spring-shaped member is in a compressed or contracted state when the ligating slide 314 is in the closed position and is in a straightened or extended state when the ligating slide 314 is in the opened position.

When activated, the FSMA actuator 320 in the form of the flat spring-shaped member moves the ligating slide 314 relative to the bracket body 312 by either straightening to move the ligating slide 314 to the opened position or by contracting to move the ligating slide 314 to the closed position. For example, in one embodiment, exposure of the FSMA actuator 320 to a magnetic field (B) or magnetic field gradient causes extension or straightening of the FSMA actuator 320 in a lengthwise direction. The ligating slide 314 is thereby moved from the closed position toward the opened position, as shown best in FIG. 15. The pin 322 may guide or control the direction of extension of the actuator 320 during movement of the ligating slide 314 between the opened position and the closed position. The bracket body 312 may further guide the sliding motion or translation of the ligating slide 314 as the FSMA actuator straightens or contracts.

Figure 12:
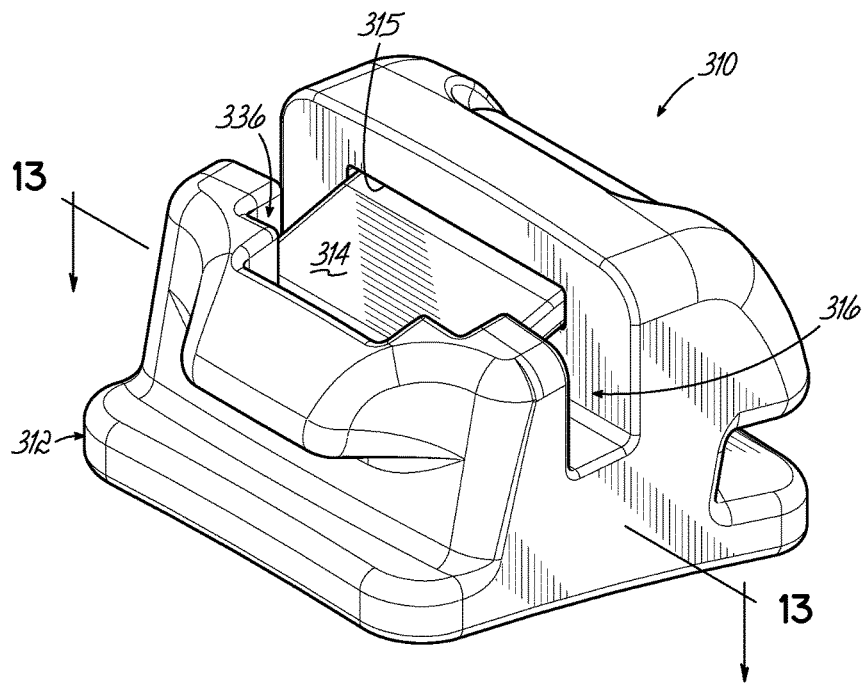
FIG. 12 is a perspective view of one embodiment of a self-ligating orthodontic bracket in accordance with the principles of the present invention.
Figure 13:
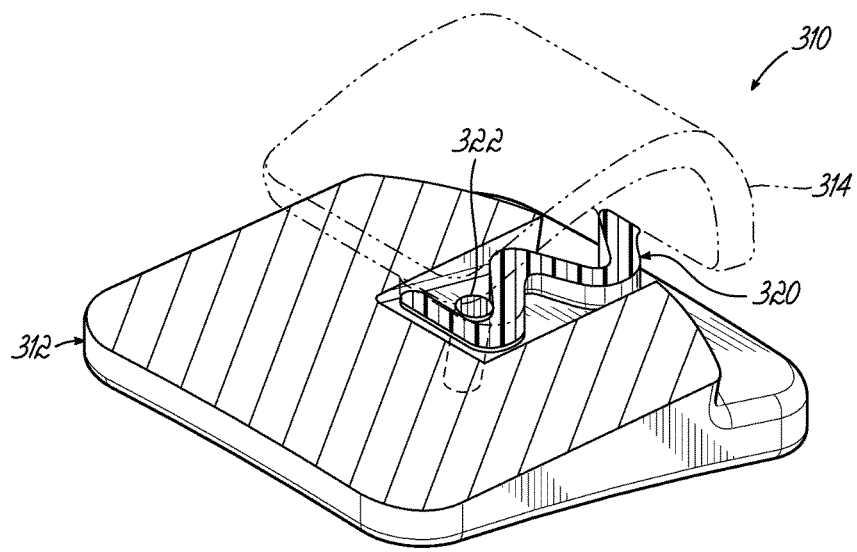
FIG. 13 is a cross-sectional view of the self-ligating orthodontic bracket of FIG. 12, taken along section line 13-13, with a movable member shown in phantom line.
Figure 14:
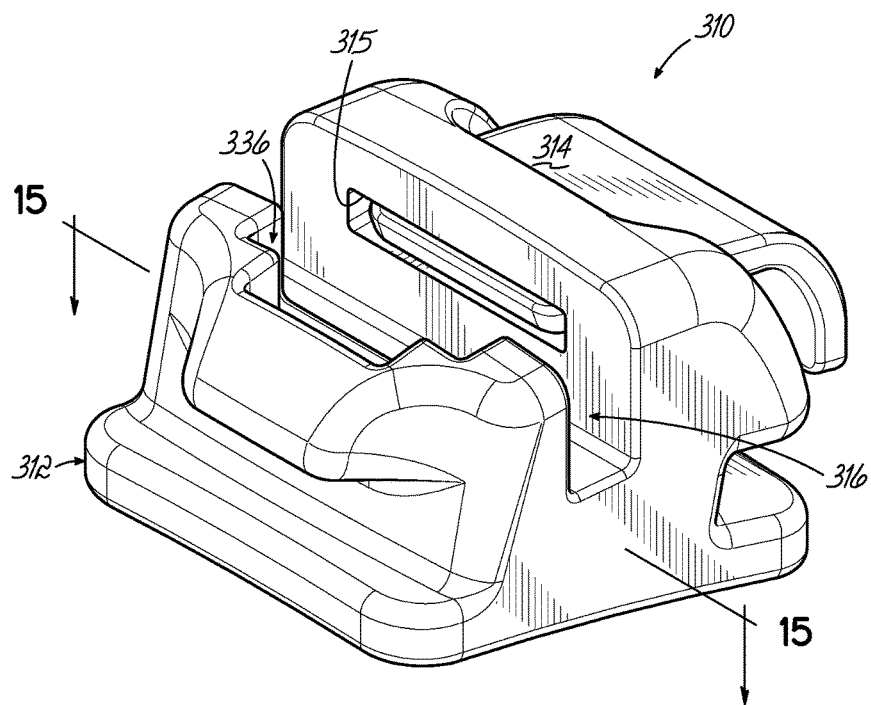
FIG. 14 is a perspective view of the self-ligating orthodontic bracket of FIG. 12, showing the movable member in an opened position.
Figure 15:
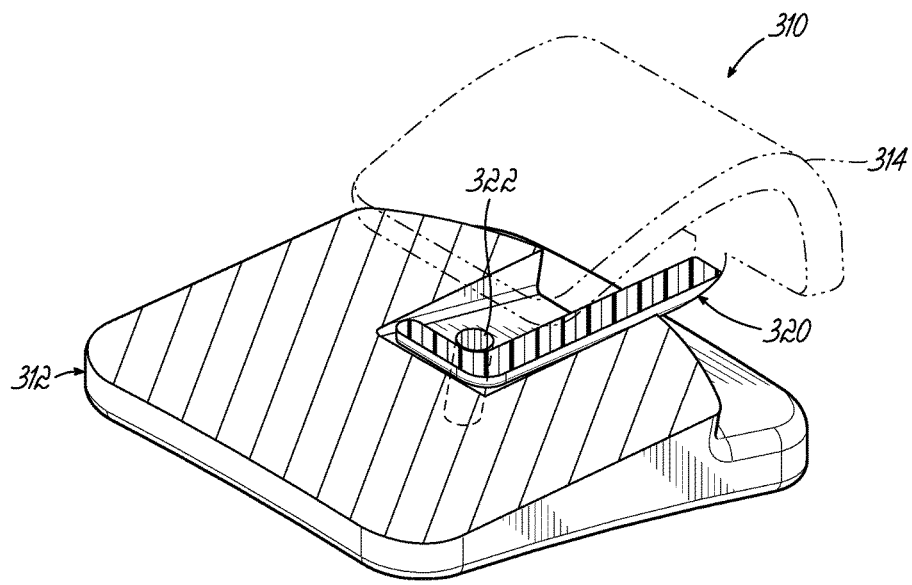
FIG. 15 is a cross-sectional view of the self-ligating orthodontic bracket of FIG. 14, taken along section line 15-15, with the movable member shown in phantom line.

Alternatively, and by way of further example, exposure of the FSMA actuator 320 to a magnetic field (B) or magnetic field gradient may cause contraction or compression of the actuator 320 from a relatively straight configuration to the stair step-like configuration shown in FIG. 13 and, consequently, movement of the ligating slide 314 from the opened position (FIG. 14) toward the closed position (FIG. 12).

Figure 16:
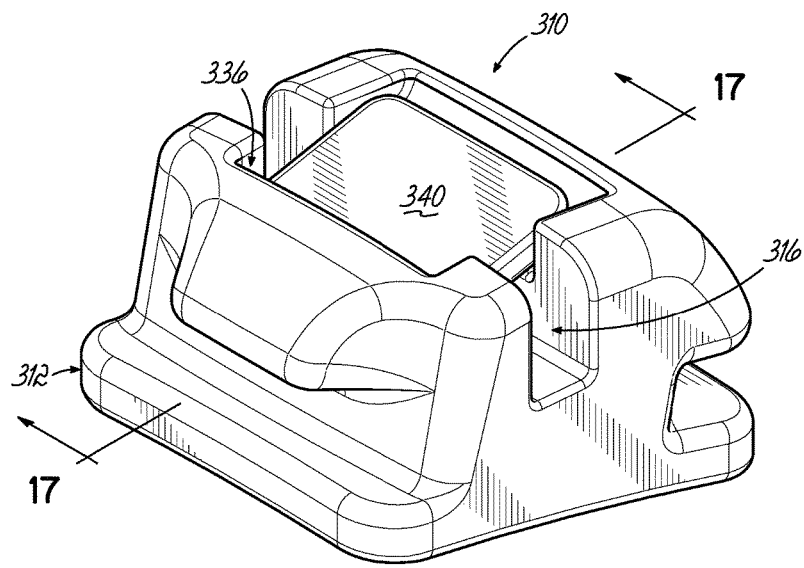
FIG. 16 is a perspective view of one embodiment of a self-ligating orthodontic bracket in accordance with the principles of the present invention.
Figure 17:
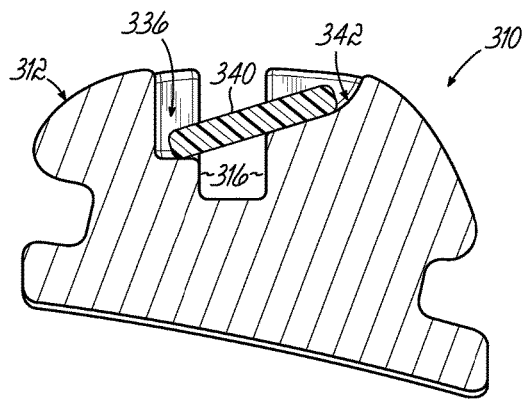
FIG. 17 is a cross-sectional view of the self-ligating orthodontic bracket of FIG. 16, taken along section line 17-17, the movable member shown in a closed position.
Figure 18:
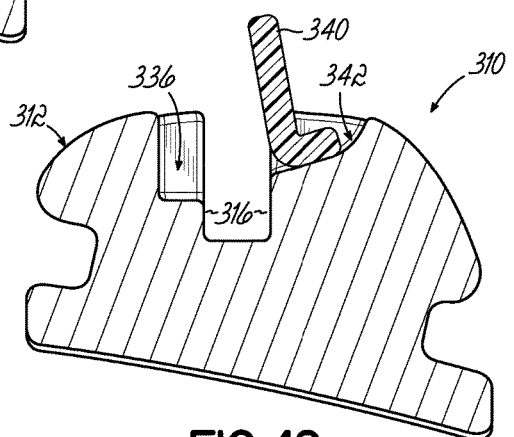
FIG. 18 is a cross-sectional view similar to FIG. 17, the movable member shown in an opened position.

With reference now to FIGS. 16-18, in which like reference numerals refer to like elements in FIGS. 12-15, in another embodiment, the self-ligating orthodontic bracket 310 includes a door-like FSMA actuator 340 coupled to the bracket body 312. A portion of the door-like actuator 340 is positioned in a groove 342 formed in the bracket body 312. The door-like actuator 340 forms the movable member and is movable from a closed position (FIGS. 16 and 17) to an opened position (FIG. 18).

In the embodiment shown in FIGS. 16-18, the actuator 340 comprises a flat, planar-like member that extends across the archwire slot 316 to the recess 336 when the door-like actuator 340 is in the closed position. It will be appreciated that a flat, planar-like member is advantageous for ease of manufacture.

Exposure of the door-like actuator 340 to a magnetic field (B) or magnetic field gradient causes the actuator 340 to change shape from the flat, planar-like configuration shown in FIG. 17 to an L-shaped configuration shown in FIG. 18. The recess 336 may be substantially deep so that when an archwire is inserted into the archwire slot 316, the archwire may extend in a labial-lingual direction labially above the recess 336. With the configuration of the actuator 340 in the closed position, the actuator 340 may actively ligate the archwire.

Figure 19:
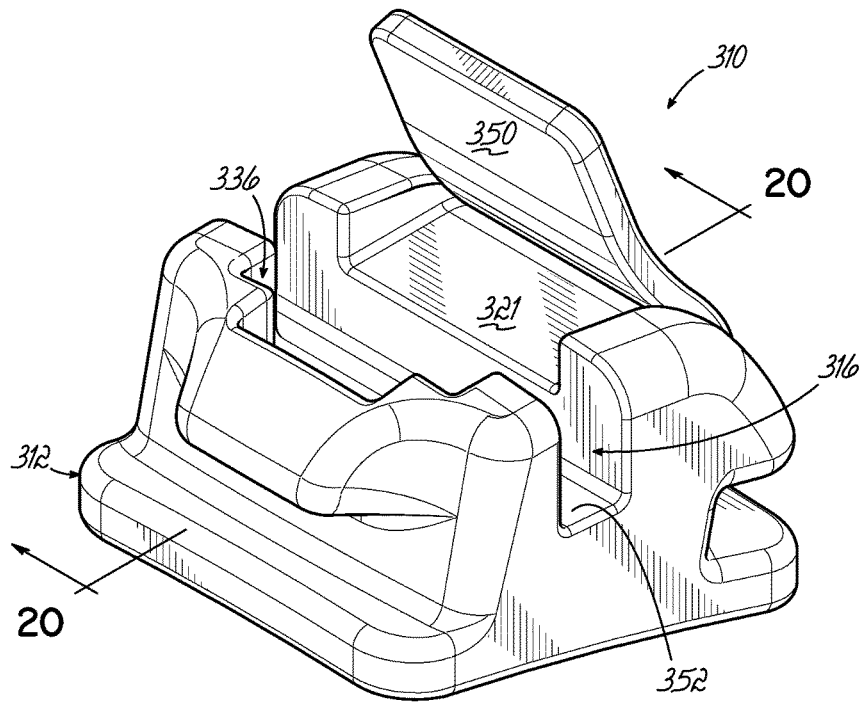
FIG. 19 is a perspective view of one embodiment of a self-ligating orthodontic bracket in accordance with the principles of the present invention.
Figure 20:
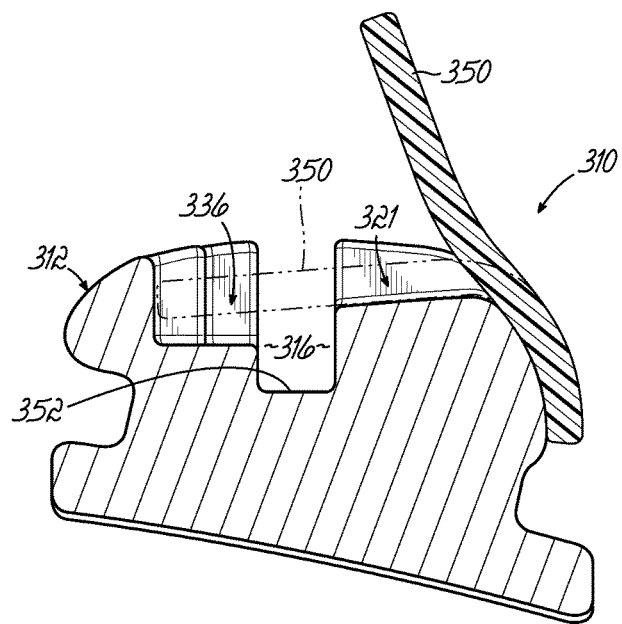
FIG. 20 is a cross-sectional view of the self-ligating orthodontic bracket of FIG. 19, taken along section line 20-20, with a movable member shown in an opened position and with the movable member shown in a closed position in phantom line.

Alternatively, and with reference to FIGS. 19 and 20, in which like reference numerals refer to like elements in FIGS. 16-18, an actuator 350 may be curved instead of being flat. For example, the actuator 350 may be contoured to conform to the surrounding surfaces of the bracket body 312 when in the closed position. Although not shown, as with other actuators, a portion of the actuator 350 may be affixed to the bracket body 312, for example, by a laser weld, press fit, or pin assembly.

In the embodiment shown, the actuator 350 may be substantially parallel to a base surface 352 of the archwire slot 316 when the actuator 350 is in the closed position (shown in phantom line). Exposure of the actuator 350 to a magnetic field (B) or magnetic field gradient may cause the actuator 350 to change curvature to the opened position from the closed position or to the closed position from the opened position depending on its normal configuration described above.

Figure 21:
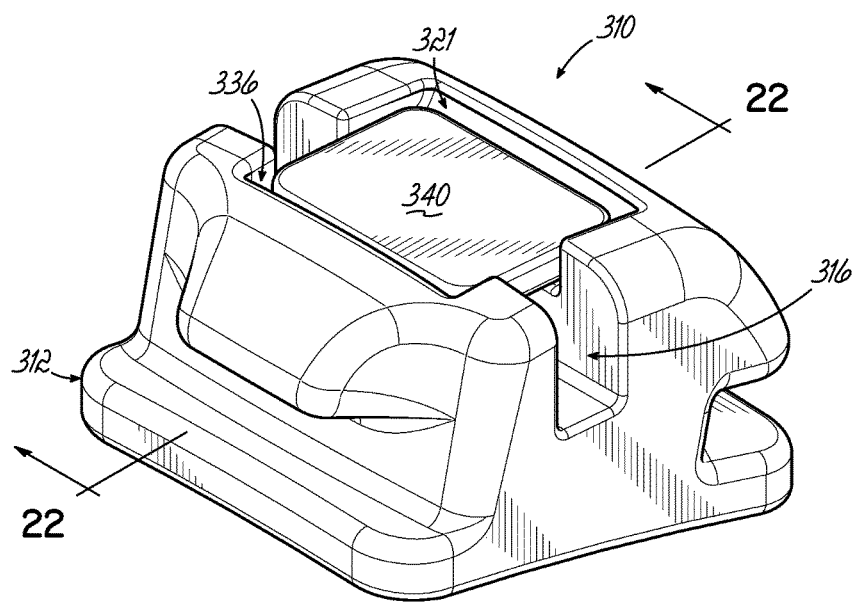
FIG. 21 is a perspective view of one embodiment of a self-ligating orthodontic bracket in accordance with the principles of the present invention.
Figure 22:
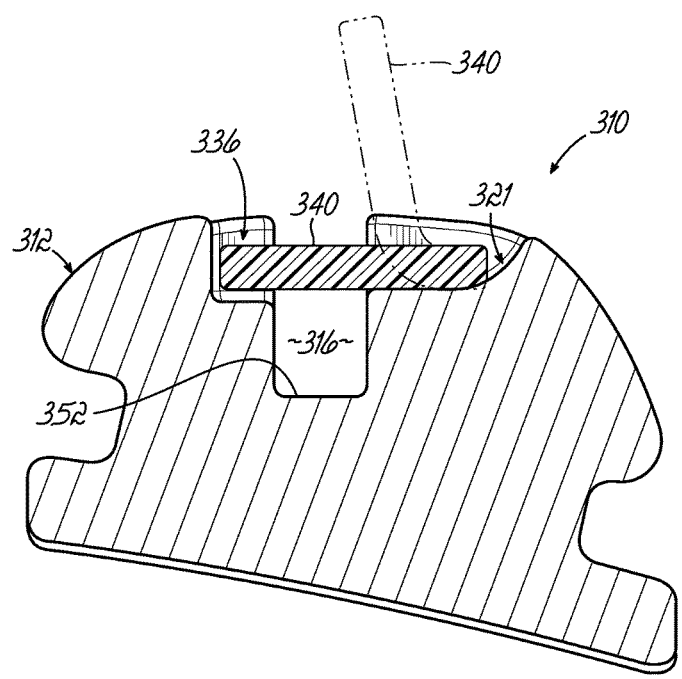
FIG. 22 is a cross-sectional view of the self-ligating orthodontic bracket of FIG. 21, taken along section line 22-22, the movable member shown in a closed position and with the movable member shown in an opened position in phantom line.

Alternatively, and with reference to FIGS. 21 and 22, in which like reference numerals refer to like elements in FIGS. 16-18, the recess 336 may be configured such that the actuator 340 may be substantially parallel to a base surface 352 of the archwire slot 316 when in the closed position. Furthermore, in contrast to the embodiment shown in FIGS. 16-18 above in which the recess 336 is relatively shallow, the actuator 340 shown in FIGS. 21 and 22 may passively ligate an archwire in the archwire slot 316. In other words the dimension from the base surface 352 of the archwire slot 316 to the outwardly facing surface of the recess 336 may be approximately equal to or greater than the dimension of the archwire. As such, the actuator 340 may form a closed lumen through which the archwire may slide during orthodontic treatment.

Figure 23:
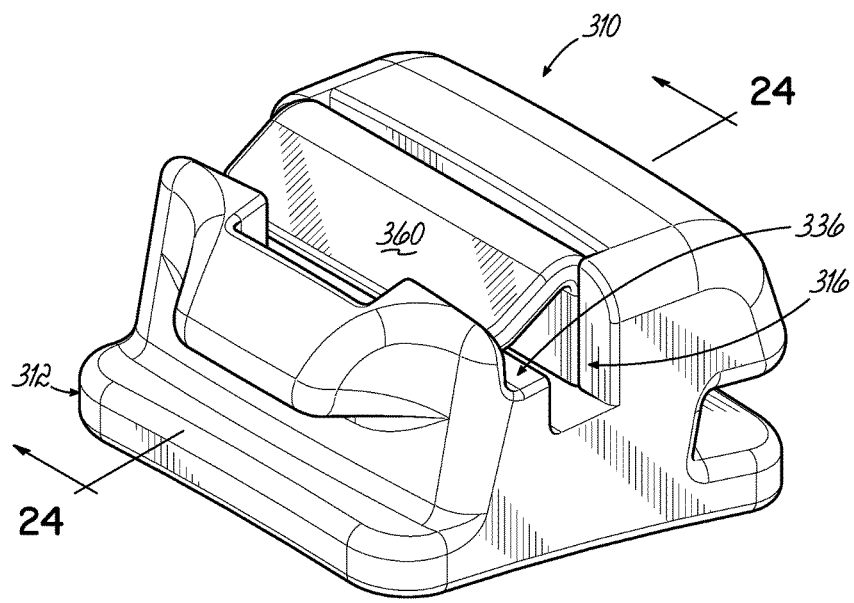
FIG. 23 is a perspective view of one embodiment of a self-ligating orthodontic bracket in accordance with the principles of the present invention.
Figure 24:
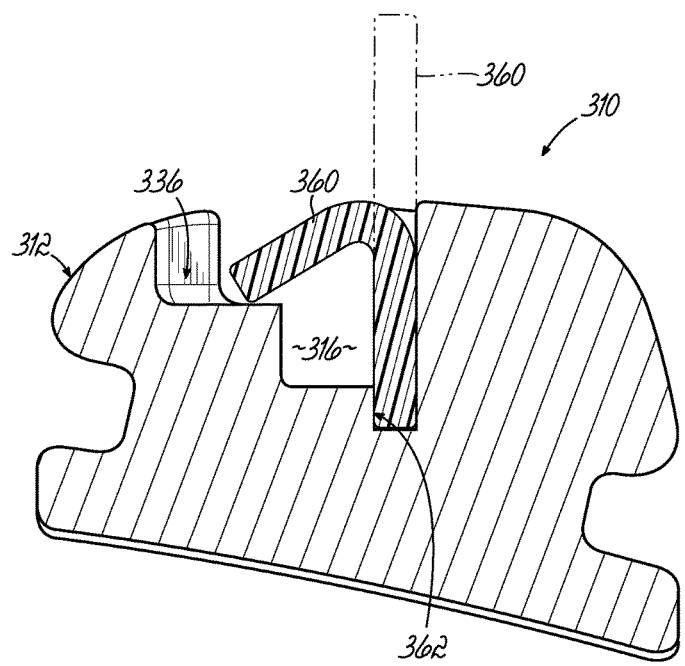
FIG. 24 is a cross-sectional view of the self-ligating orthodontic bracket of FIG. 23, taken along section line 24-24, with the movable member in a closed position and with the movable member shown in an opened position in phantom line.

Referring now to FIGS. 23 and 24, in another embodiment in which like reference numerals refer to like elements in FIGS. 16-20, the self-ligating orthodontic bracket 310 includes a door-like FSMA actuator 360. The bracket body 312 includes a pocket 362 which may be recessed into one surface of the archwire slot 316. The door-like actuator 360 may be secured in the pocket 362 and form at least a portion of a sidewall of the archwire slot 316.

In one embodiment, and as best shown in FIG. 24, the actuator 360 comprises a planar-like configuration in the open position (shown in phantom line). As with other FSMA actuators described herein, the door-like FSMA actuator 360 is movable between an opened position, shown in phantom in FIG. 24, and a closed position in which the archwire is retained within the archwire slot 316. In this regard, only a portion of the FSMA actuator 360 may move. The actuator 360 may bend or fold in a lengthwise manner that is generally parallel to the archwire slot 316.

Exposure of the actuator 360 to a magnetic field (B) or magnetic field gradient causes the actuator 360 to change shape. For example, the actuator 360 may change from the planar-like configuration to an L-shaped configuration such that a portion of the actuator 360 extends across the archwire slot 316 into the recess 336 in the closed position. The reverse arrangement is also contemplated in which the actuator 360 changes shape from the L-shaped configuration to the planar-like configuration on exposure to a magnetic field (B) or a magnetic field gradient.

Figure 25:
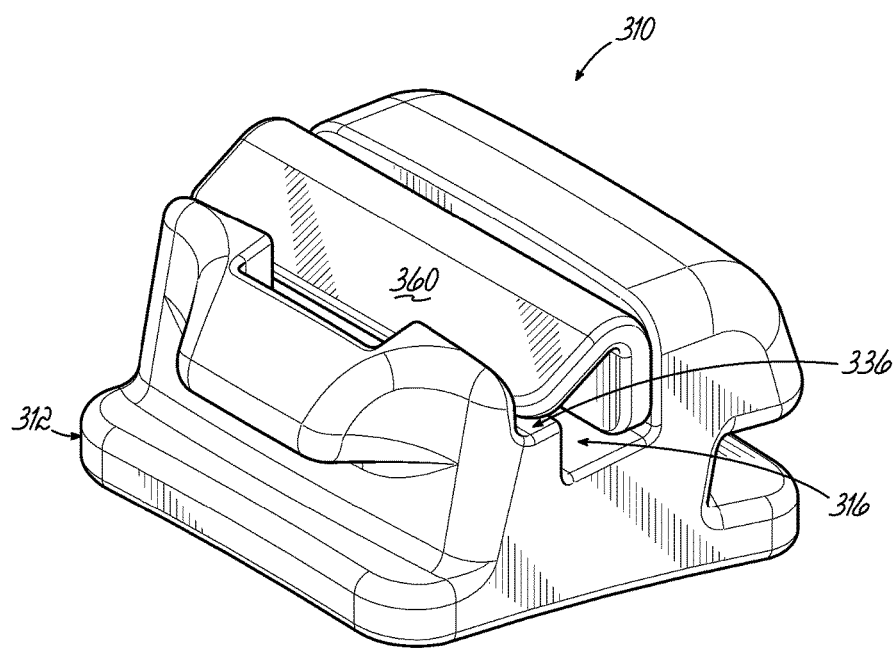
FIG. 25 is a perspective view of one embodiment of a self-ligating orthodontic bracket in accordance with the principles of the present invention.

In one embodiment shown in FIG. 25, the pocket 362 may extend the full length of the archwire slot 316. The FSMA actuator 360 may also extend the full mesial-distal width of the archwire slot 316 and so form one complete sidewall of the archwire slot 316.

Figure 26:
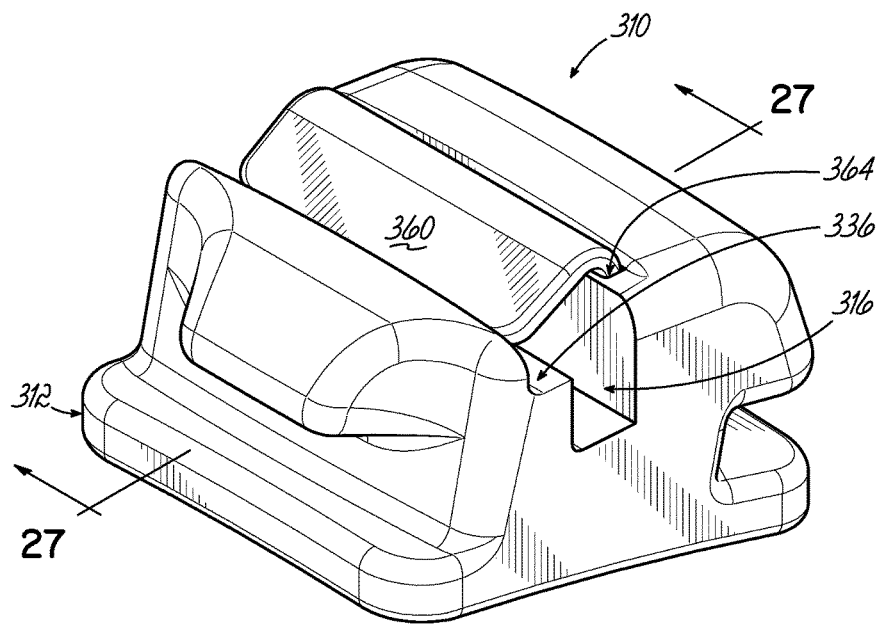
FIG. 26 is a perspective view of one embodiment of a self-ligating orthodontic bracket in accordance with the principles of the present invention.
Figure 27:
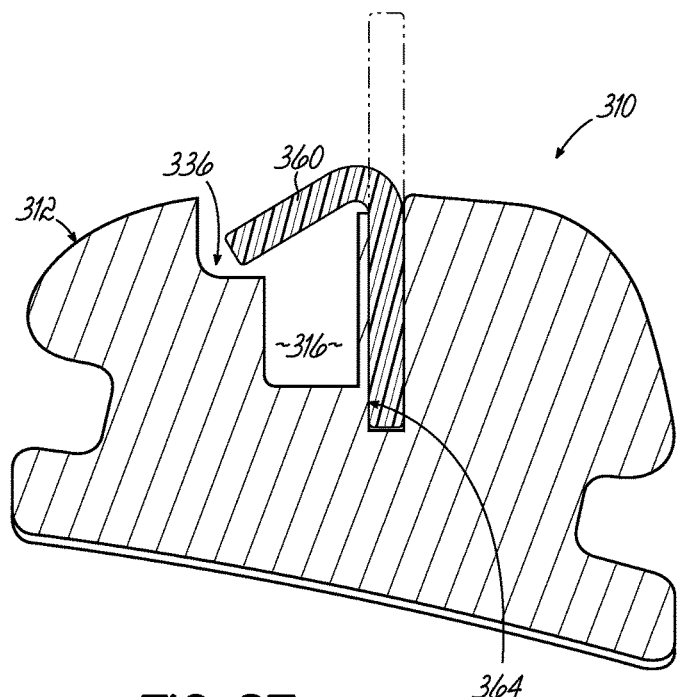
FIG. 27 is a cross-sectional view of the self-ligating orthodontic bracket of FIG. 26, taken along section line 27-27, with the movable member in a closed position and with the movable member shown in an opened position in phantom line.

Referring now to FIGS. 26 and 27, in another embodiment, in which like reference numerals refer to like elements in FIGS. 23-25, a pocket 364 is spaced apart from the sidewall surface of the archwire slot 316. The actuator 360 is secured within the pocket 364 and therefore does not form any portion of either sidewall of the archwire slot 316.

In one embodiment, and as best shown in FIG. 27, the actuator 360 comprises a planar-like configuration in the open position (shown in phantom line). Exposure of the actuator 360 to a magnetic field (B) or magnetic field gradient causes the actuator 360 to change shape or fold to an L-shaped configuration such that a portion of the actuator 360 extends across the archwire slot 316. The folded portion of the actuator 360 may be received in the recess 336 in the closed position.

With reference now to FIGS. 28-35, in one embodiment, a self-ligating orthodontic bracket 410 includes a base member 412 and a movable member including the rotatable member 414. The rotatable member 414 is coupled to the base member 412 via an FSMA actuator 420.

The base member 412 is configured to be attached to a tooth and includes an archwire slot 416 formed therein that is configured to receive an archwire (not shown) for applying corrective forces to the tooth. The base member 412 includes a slot 421 and an internal bore 425 into which the FSMA actuator 420 is secured (shown, for example, in FIG. 30).

The rotatable member 414 is configured to cooperate with the base member 412 and rotate about an axis oriented generally transversely (e.g., perpendicularly) to the tooth surface and to the base member 412. The rotatable member 414 includes a bore 423 that is generally aligned with slot 421 and receives one end of the FSMA actuator 420 during the full range of motion of the rotatable member 414.

The rotatable member 414 has at least two positions relative to the base member 412. In one position, the rotatable member 414 leaves the archwire slot 416 open (shown in FIG. 34) in which an archwire (not shown) may be inserted or removed from the archwire slot 414. In at least one other position, shown for example in FIG. 28, the rotatable member 414 captures an archwire in the archwire slot to effectuate orthodontic treatment.

Figure 31:
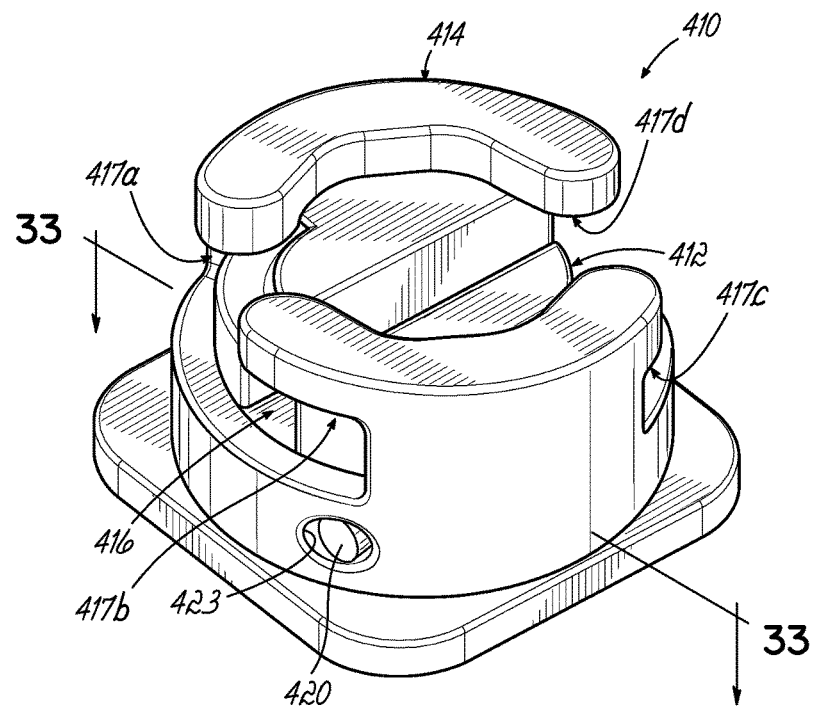
FIG. 31 is a perspective view of the self-ligating orthodontic bracket of FIG. 28, with the movable member shown in a second closed position.
Figure 32:
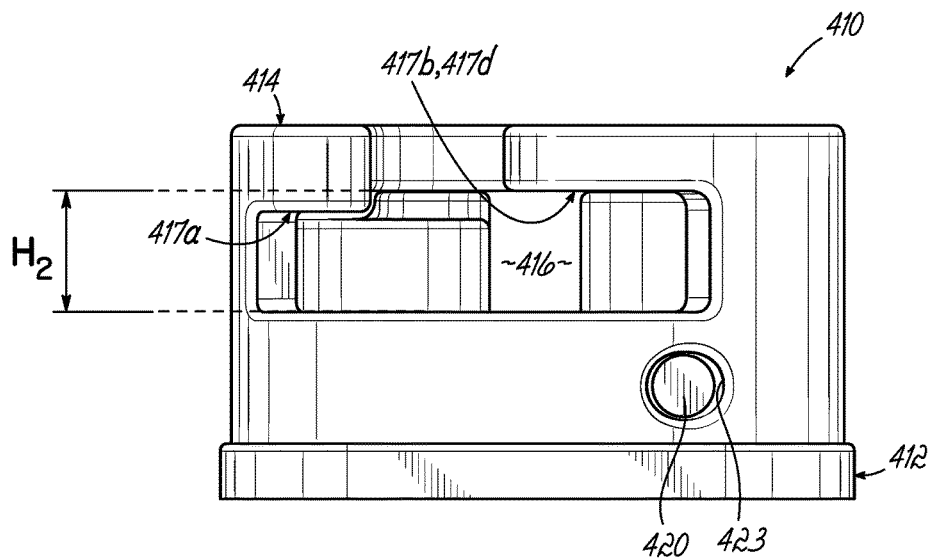
FIG. 32 is a side elevation view of the self-ligating orthodontic bracket of FIG. 31.

In one embodiment, the rotatable member 414 has at least two closed positions in which the rotatable member 414 captures an archwire in the archwire slot 416. For example, the rotatable member 414 may be rotated between at least any two positions. This may include rotation between any two of an opened position (FIG. 34), a first closed position (FIGS. 28 and 29), and a second closed position (FIGS. 31 and 32). In one embodiment, the first and second closed positions differ in the dimensions of the closed lumen formed by the rotating member 414 and the base member 412. The difference in dimensions in the closed lumen may provide passive and/or active ligation of the archwire.

Figure 29:
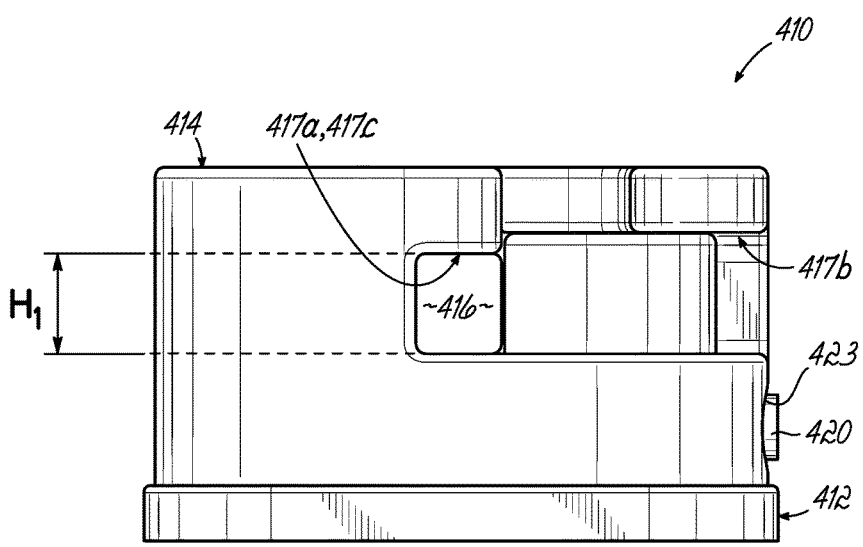
FIG. 29 is a side elevation view of the self-ligating orthodontic bracket of FIG. 28, the movable member shown in a closed position.

To that end, in one embodiment, the rotatable member 414 may include cutouts 417a, 417b, 417c, and 417d. Rotation of the rotatable member 414 between opened and closed positions locates the cutouts 417a and 417c or 417b and 417d relative to the archwire slot 416. Cutouts 417a and 417c or 417b and 417d provide different labial-lingual dimensions of the archwire slot 416 for facilitating different first and second lumen heights $H_1$, $H_2$, respectively, as shown in FIGS. 29 and 32.

The FSMA actuator 420 (shown best in FIGS. 30, 33, and 35) couples the rotatable member 414 to the base member 412, and may rotate the rotatable member 414 about the axis of rotation when exposed to a magnetic field (B) or a magnetic field gradient. The FSMA actuator 420 may be a cylindrical elongate member and have an L-shape (shown in FIG. 33) in one of the opened or closed positions and may be generally straight (shown in FIG. 30) in the other of the opened and closed positions. Alternatively, the FSMA actuator 420 may have an intermediate configuration shown in FIG. 35, which aligns the rotatable member 414 with the base member 412 in one position, such as, in the opened position shown in FIG. 34.

Figure 30:
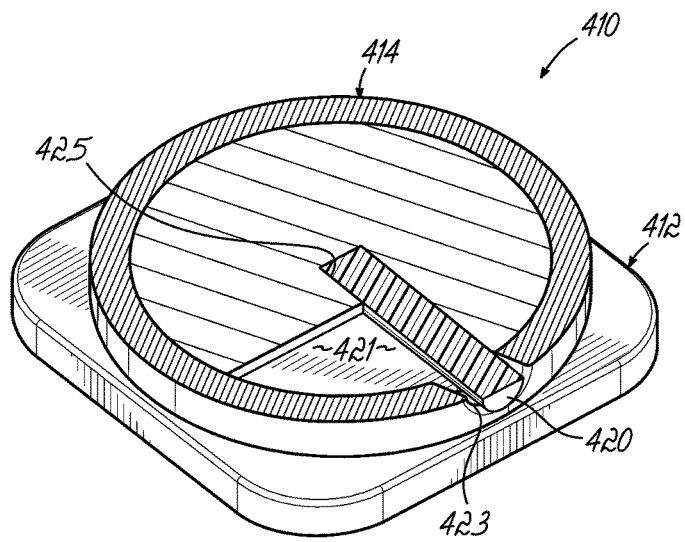
FIG. 30 is a cross-sectional view of the self-ligating orthodontic bracket of FIG. 28, taken along section line 30-30.
Figure 33:
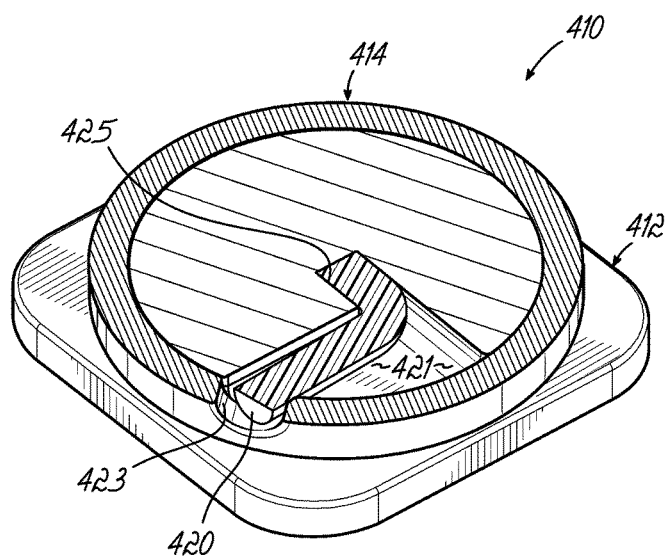
FIG. 33 is a cross-sectional view of the self-ligating orthodontic bracket of FIG. 31, taken along section line 33-33.
Figure 34:
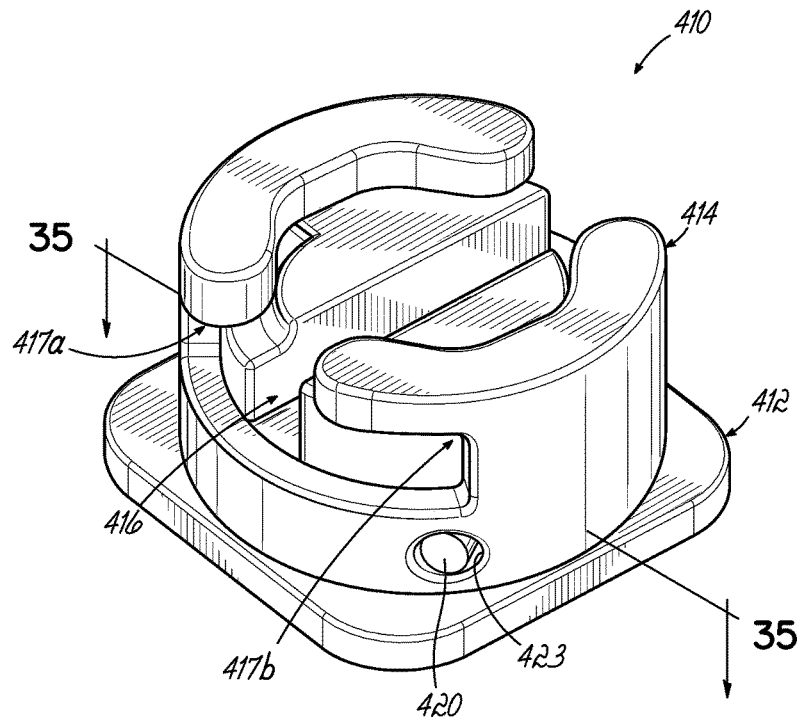
FIG. 34 is a perspective view of the self-ligating orthodontic bracket of FIG. 28, with the movable member shown in an opened position.
Figure 35:
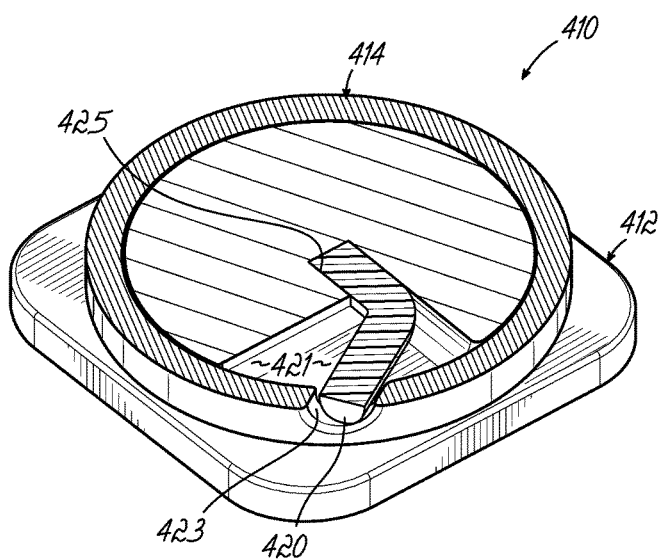
FIG. 35 is a cross-sectional view of the self-ligating orthodontic bracket of FIG. 34, taken along section line 35-35.
Figure 36:
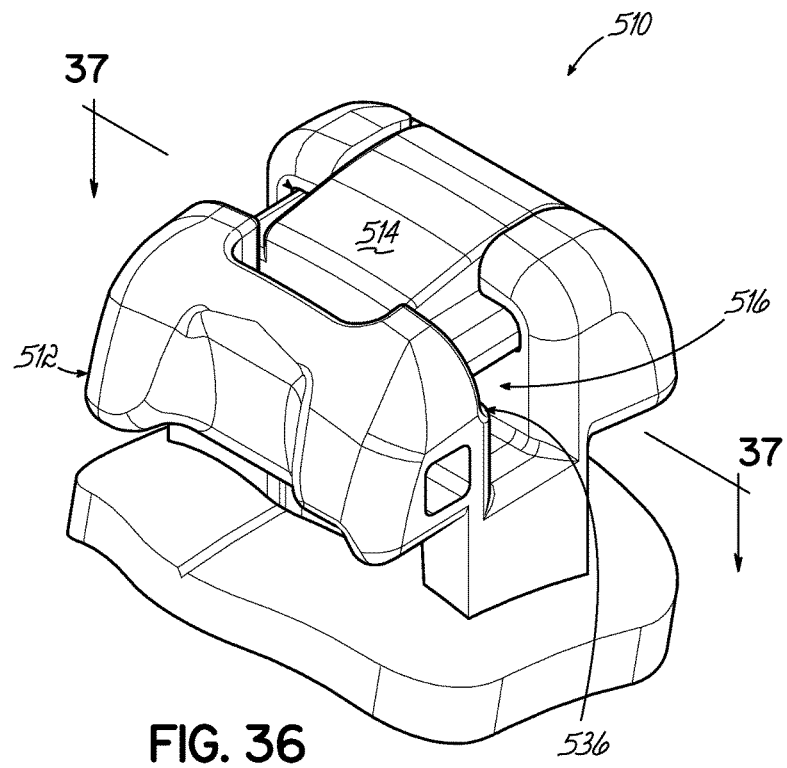
FIG. 36 is a perspective view of one embodiment of a self-ligating orthodontic bracket in accordance with the principles of the present invention.

When exposed to a magnetic field (B) or a magnetic field gradient, the FSMA actuator 420 changes shape and, consequently, rotates the rotatable member 414 relative to the base member 412. The shape change may be between any two configurations shown in FIGS. 30, 33, and 35. For example, in one embodiment, exposure of the FSMA actuator 420 to a magnetic field (B) or a magnetic field gradient causes the FSMA actuator 420 to change shape from a straight configuration, as best shown in FIG. 30, to an L-shaped configuration, as best shown in FIG. 33, and, consequently, rotation of the rotatable member 414 from a closed position (FIG. 28) to the other closed position (FIG. 31). Alternatively, exposure of the FSMA actuator 420 to a magnetic field (B) or a magnetic field gradient may cause the actuator 420 to change shape from the straight configuration to the intermediate configuration shown in FIG. 35 and the opened position shown in FIG. 34.

It will be appreciated that the FSMA actuator 420 may change shape from a straight configuration to an L-shaped configuration, from a straight configuration to an intermediate shaped configuration, or from an intermediate configuration to an L-shaped configuration to rotate the rotatable member 414 from a first closed position toward a second closed position or from the second closed position toward the opened position. The reverse shape change between any two of the above configurations is also contemplated. That is, from the L-shaped configuration to either of the straight configuration or the intermediate configuration. This may depend upon whether the orthodontic bracket 410 is normally opened or is normally closed.

Furthermore, when the FSMA actuator 420 is exposed to a magnetic field (B), the slot 421 guides the FSMA actuator 420 as it changes shape. In this regard, the slot 421 constrains movement or the shape change in a plane and may provide outer limits for the movement of the FSMA actuator 420. When the FSMA actuator 420 abuts the end walls of the slot 421, no further movement is possible. The end walls of the slot 421 may therefore determine when the rotatable member 414 is in the opened position and when the actuator 420 is in a closed position.

For example, when the FSMA actuator 420 abuts a first end of the slot 421, as shown in FIG. 30, the rotatable member 414 may be in a first closed position (FIG. 28), and when the actuator 420 abuts the second end of the slot 421, as shown in FIG. 33, the rotatable member 414 may be in a second closed position (FIG. 31). The positions of the FSMA actuator 420 in the slot 421 are combined with the cutouts 417a, 417b, 417c, and 417d (described above) to provide passive ligation or active ligation of an archwire, or opening of the archwire slot 416 while positioning the rotatable member 414 through the use of a magnetic field (B) or a magnetic field gradient.

Figure 28:
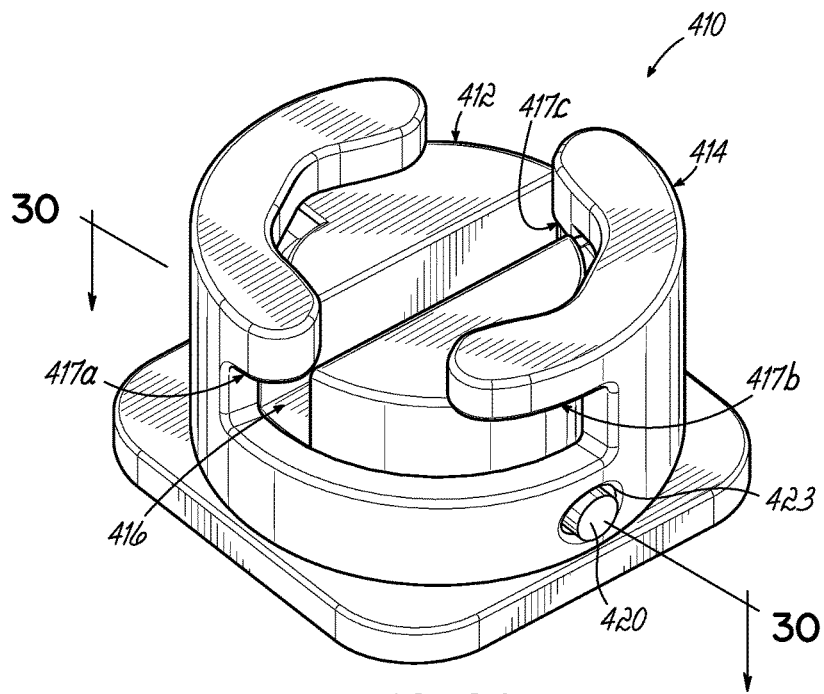
FIG. 28 is a perspective view of one embodiment of a self-ligating orthodontic bracket in accordance with the principles of the present invention.

In particular, in an exemplary embodiment, as is shown in FIGS. 28-30, cutouts 417a and 417c may cooperate with the archwire slot 416 to provide a first lumen height $H_1$ in the first closed position when the FSMA actuator 420 is straight. With reference to FIGS. 31-33, cutouts 417b and 417d may cooperate with the archwire slot 416 to provide a second lumen height $H_2$ in the second closed position when the FSMA actuator 420 is L-shaped. As such, the rotatable member 414 may provide first and second closed positions presenting first and second lumen heights $H_1$, $H_2$, as shown in FIGS. 29 and 32. In this embodiment, a clinician may adjust the ligation forces during treatment without changing the archwire. That is, the clinician may select active or passive ligation without changing the archwire and without manipulating the rotatable member 414 by hand.

Figure 37:
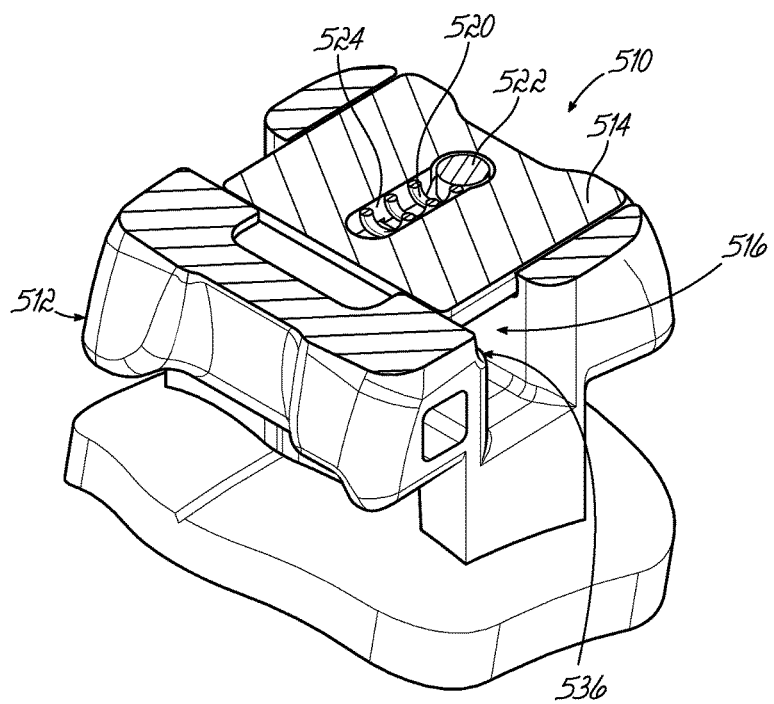
FIG. 37 is a cross-sectional view of the self-ligating orthodontic bracket of FIG. 36, taken along section line 37-37.
Figure 38:
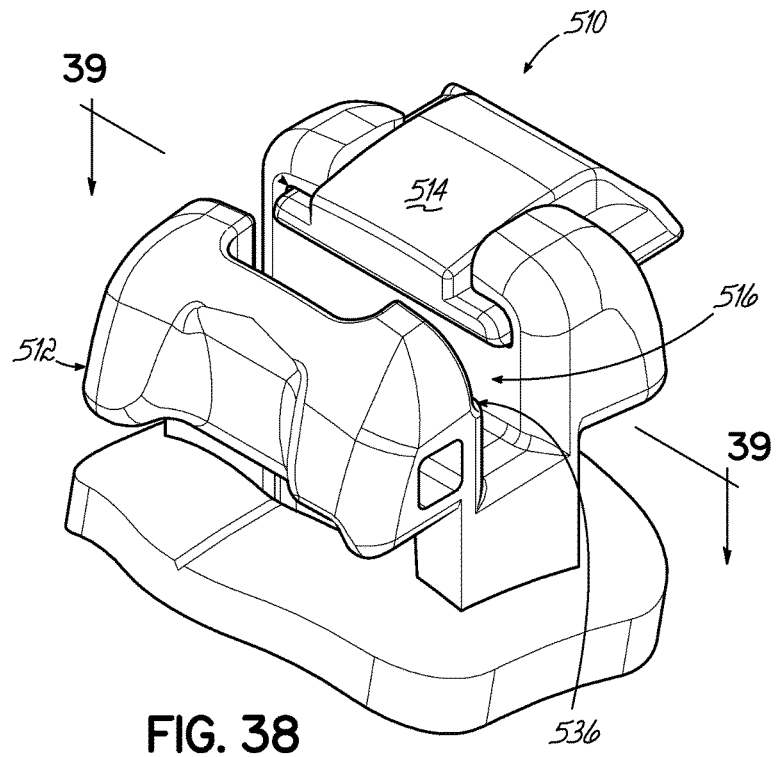
FIG. 38 is a perspective view of the self-ligating orthodontic bracket of FIG. 36, with the movable member shown in an opened position.

With reference now to FIGS. 36-39, in one embodiment, a self-ligating orthodontic bracket 510 includes a bracket body 512 and a movable member, such as, a ligating slide 514 coupled to the bracket body 512. The bracket body 512 includes an archwire slot 516 formed therein that is configured to receive an archwire (not shown). The orthodontic bracket 510 includes an FSMA actuator 520 positioned to move the ligating slide 514 when exposed to a magnetic field (B) or a magnetic field gradient. The ligating slide 514 is movable between a closed position (FIG. 36) and an opened position (FIG. 38). In the closed position, a portion of the ligating slide 514 may be positioned within a recess 536 provided in the bracket body 512.

Figure 39:
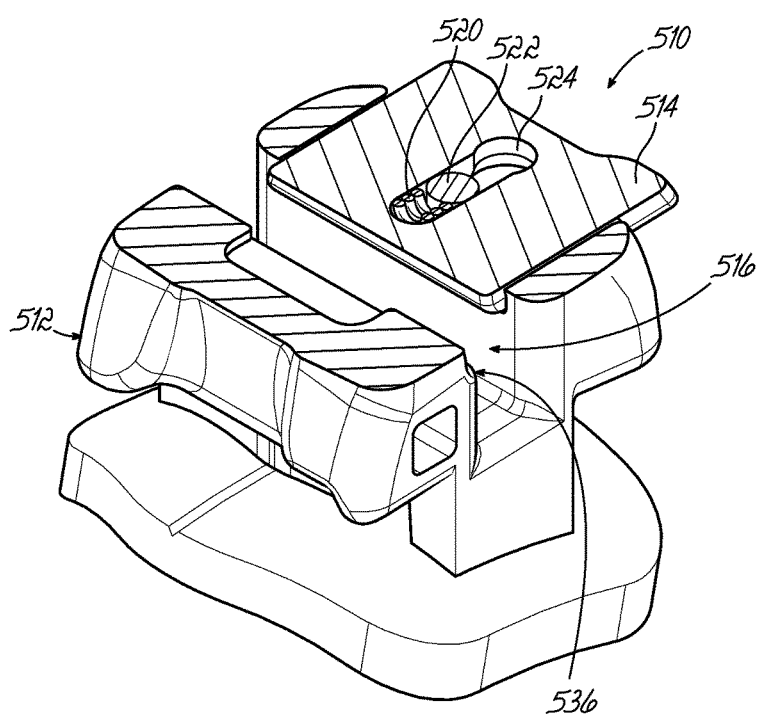
FIG. 39 is a cross-sectional view of the self-ligating orthodontic bracket of FIG. 38, taken along section line 39-39.

The ligating slide 514 may include a groove 524 that is externally inaccessible. The FSMA actuator 520 may be coupled to one or both of the bracket body 512 and the ligating slide 514 in the groove 524. For example, a pin 522 may secure one end of the actuator 520 to the ligating slide 514. In the exemplary embodiment shown, the actuator 520 is in the shape of a coil member that is sandwiched in the groove 524 between the pin 522 and the ligating slide 514 as best shown in FIGS. 37 and 39. The orthodontic bracket 510 may be similar to that described above with reference to FIGS. 3-5.

The FSMA actuator 520 may have a normally opened or normally closed configuration. As set forth above, exposure of the actuator 520 to a magnetic field (B) or a magnetic field gradient may move the ligating slide 514 from the normal position to the other position. For example, exposure to the magnetic field (B) or magnetic field gradient may cause movement from a normally closed position to an opened position. It will be appreciated that the reverse movement, that is, from a normally opened position to a closed position, is also contemplated.

In one embodiment, during use, when the FSMA actuator 520 is exposed to a magnetic field (B) or magnetic field gradient, the actuator 520 moves the ligating slide 514 relative to the bracket body 512. For example, in one embodiment shown in FIGS. 36 and 37, the FSMA actuator 520 is in a normally expanded configuration so the orthodontic bracket 510 has a normally closed configuration in which the ligating slide 514 covers the archwire slot 516, as best shown in FIG. 37. Exposure of the FSMA actuator 520 to a magnetic field (B) or magnetic field gradient causes the FSMA actuator 520 to contract or compress, as best shown in FIG. 39 and, in doing so, moves the ligating slide 514 to the opened position. The reverse movement is obtained when the magnetic field (B) or magnetic field gradient is removed. Thus, in this embodiment, the ligating slide 514 has a normally closed position. The bracket body 512 may guide the sliding motion or translation of the ligating slide 514 as is known, for example, from U.S. Pat. No. 8,033,824 disclosed above.

Figure 40:
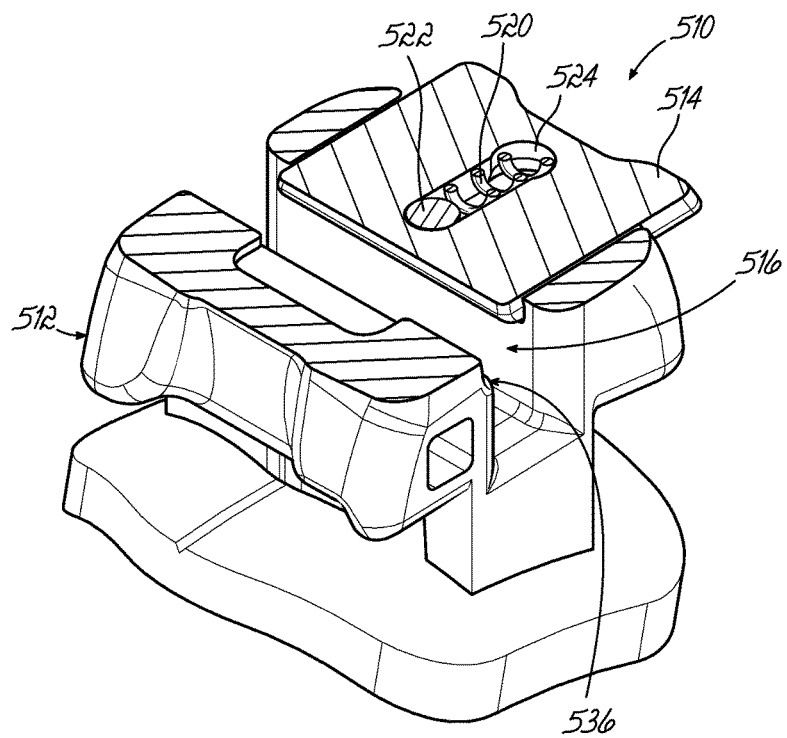
FIG. 40 is a cross-sectional view of one embodiment of a self-ligating orthodontic bracket in accordance with the principles of the present invention.
Figure 41:
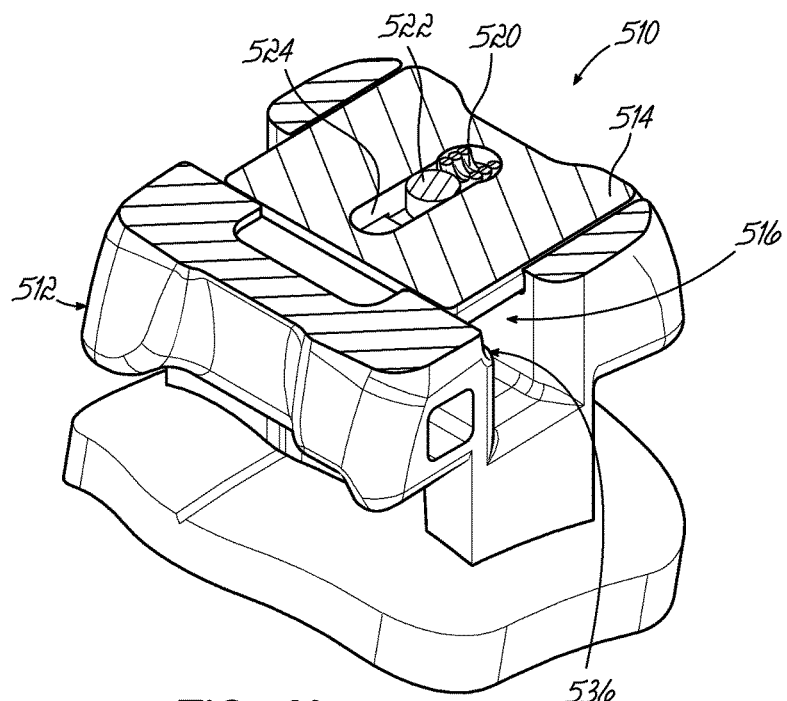
FIG. 41 is a cross-sectional view of the self-ligating orthodontic bracket of FIG. 40, with the movable member shown in a closed position.
Figure 42:
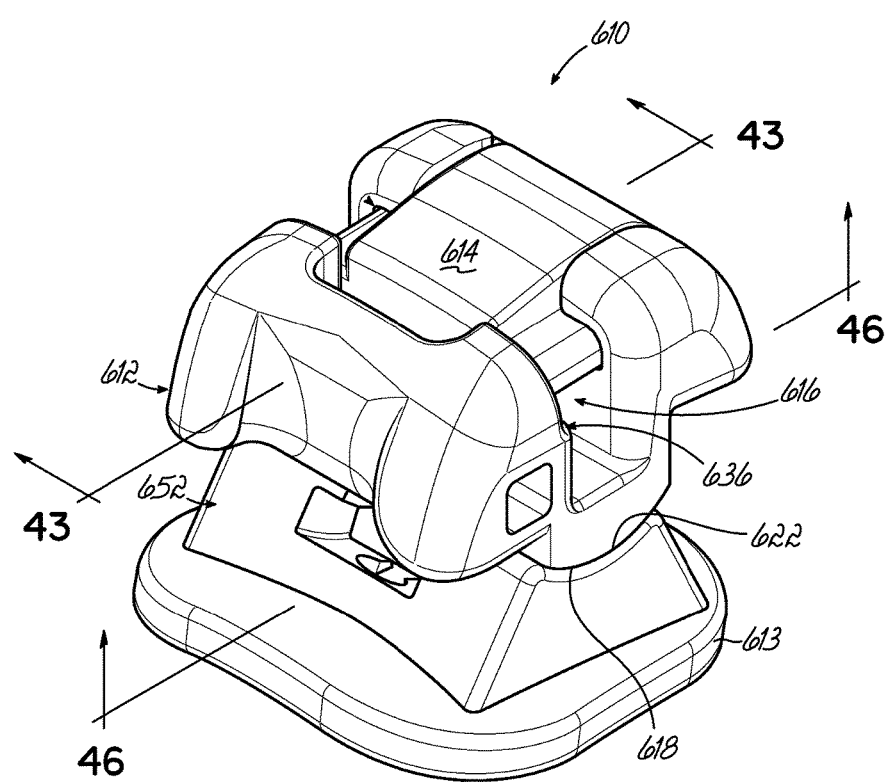
FIG. 42 is a perspective view of one embodiment of a self-ligating orthodontic bracket in accordance with the principles of the present invention.

In another embodiment, as shown in FIGS. 40 and 41, the ligating slide 514 has a normally opened position. The FSMA actuator 520 may be positioned on the rear side of the pin 522 such that exposure of the FSMA actuator 520 to a magnetic field (B) or magnetic field gradient causes the FSMA actuator 520 to compress and, consequently, move the ligating slide 514 from the opened position toward the closed position. It will be appreciated that the normally open or normally closed configuration may depend upon whether the actuator 520 is normally expanded or contracted in the absence of a magnetic field (B) or magnetic field gradient and may also depend upon placement of the actuator 520 relative to the pin 522.

With reference now to FIGS. 42-48, in one embodiment, a self-ligating orthodontic bracket 610 includes a bracket body 612 and a movable member, such as, a ligating slide 614, coupled to the bracket body 612. The bracket body 612 includes an archwire slot 616. The ligating slide 614 is slidably movable between an opened position and a closed position. The ligating slide 614 may be movable with an FSMA actuator, as previously discussed with reference to FIGS. 3-5 and 36-41.

In addition, the bracket body 612 is pivotably coupled to a base member 613. In one embodiment, the bracket body 612 may be rotated relative to the base member 613 about an axis 60% that is generally parallel to a tooth surface when the base member 613 is secured to a tooth. The bracket body 612 may be moved to adjust the torque produced by the orthodontic bracket 610 on the tooth. It will be appreciated that movement of the bracket body 612 relative to the base member 613 varies the relationship of the archwire slot 616 relative to the base member 613 and so adjusts the torque produced by the orthodontic bracket 610 on the tooth.

In this regard, the bracket body 612 and the base member 613 may include complementary contoured surfaces 618, 622. The surfaces 618, 622 slidably cooperate with one another. By this sliding motion, the bracket body 612 may be pivoted relative to the base member 613 during orthodontic treatment.

To restrict uncontrolled relative movement between the bracket body 612 and the base member 613, the orthodontic bracket 610 includes a locking system 652 by which the bracket body 612 is locked in position relative to the base member 613 once the relative position of the bracket body 612 is selected. When activated, the locking system 652 prevents relative movement between the contoured surfaces 618, 622.

With reference now to FIGS. 43-48, in one embodiment, the locking system 652 includes an FSMA actuator 620 in the form of a spring pin in one of the bracket body 612 and the base member 613. The spring pin may have a general cylindrical configuration and include a slot through the side wall that extends the length thereof. And, in the other of the bracket body 612 and the base member 613, the locking system 652 further includes a retaining slot 625 that receives the FSMA spring pin 620 therein.

Figure 43:
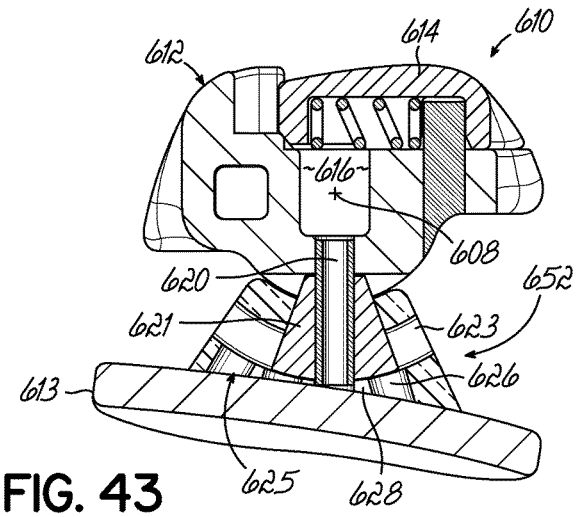
FIGS. 43-45 are cross-sectional views of the self-ligating orthodontic bracket of FIG. 42, taken along section line 43-43, with a pivotable member shown in various angular positions.
Figure 44:
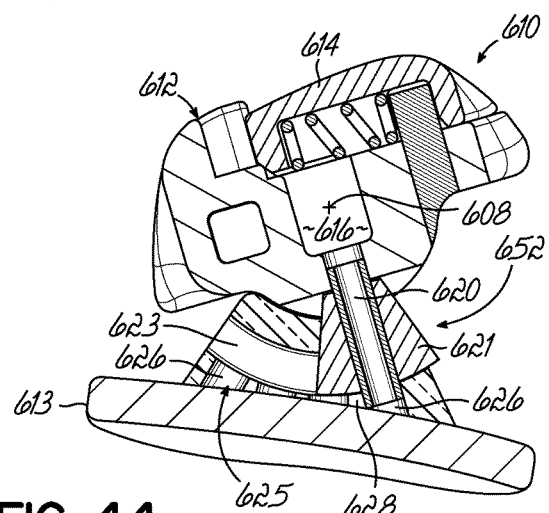
Figure 45:
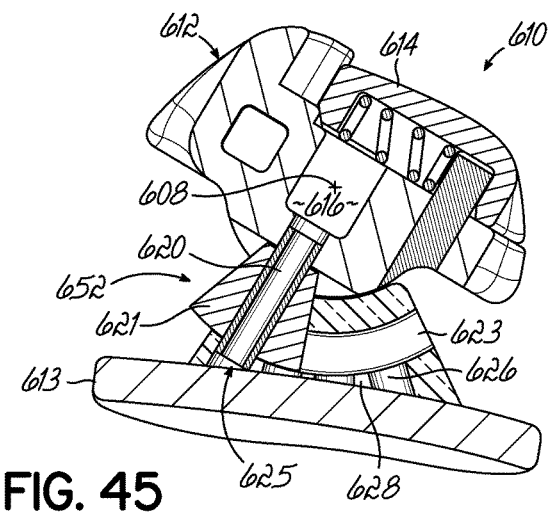

With specific reference to FIGS. 43-45, in which an exemplary embodiment is shown in various torque positions, the locking system 652 includes a rocker 621 that supports the spring pin 620, and the base member 613 includes a track 623 that defines the retaining slot 625. The rocker 621 slides within the track 623 as the contoured surfaces 618, 622 slide relative to one another. The spring pin 620 cooperates with the retaining slot 625 to define a range of various preselected, fixed torque positions.

Figures 46, 47:
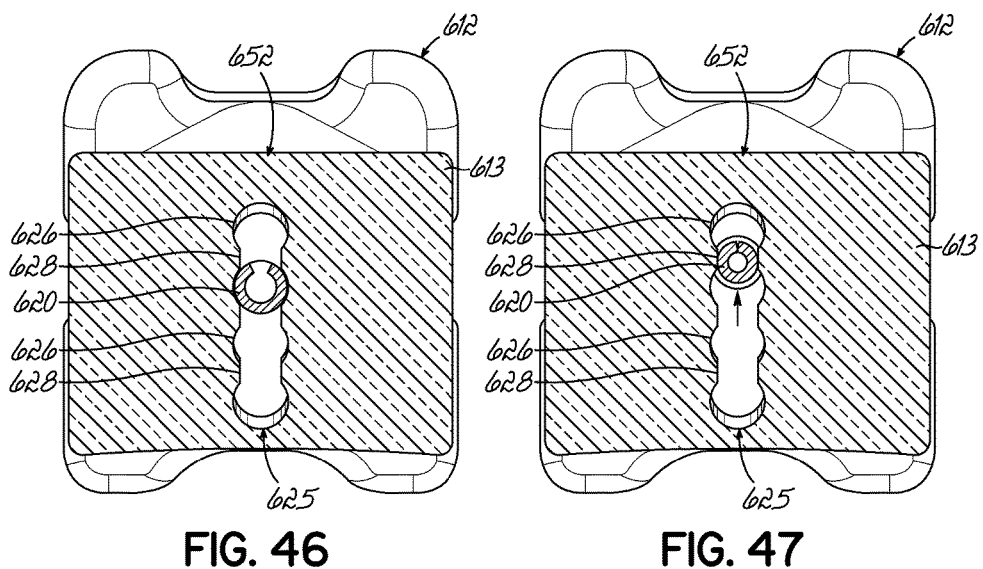
FIGS. 46-48 are cross-sectional views of the self-ligating orthodontic bracket of FIG. 42, taken along line section 46-46, showing a spring pin in various positions.
Figure 48:
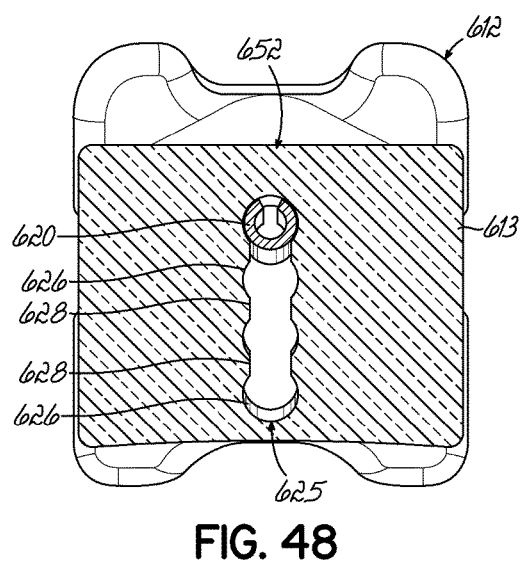
Figure 49:
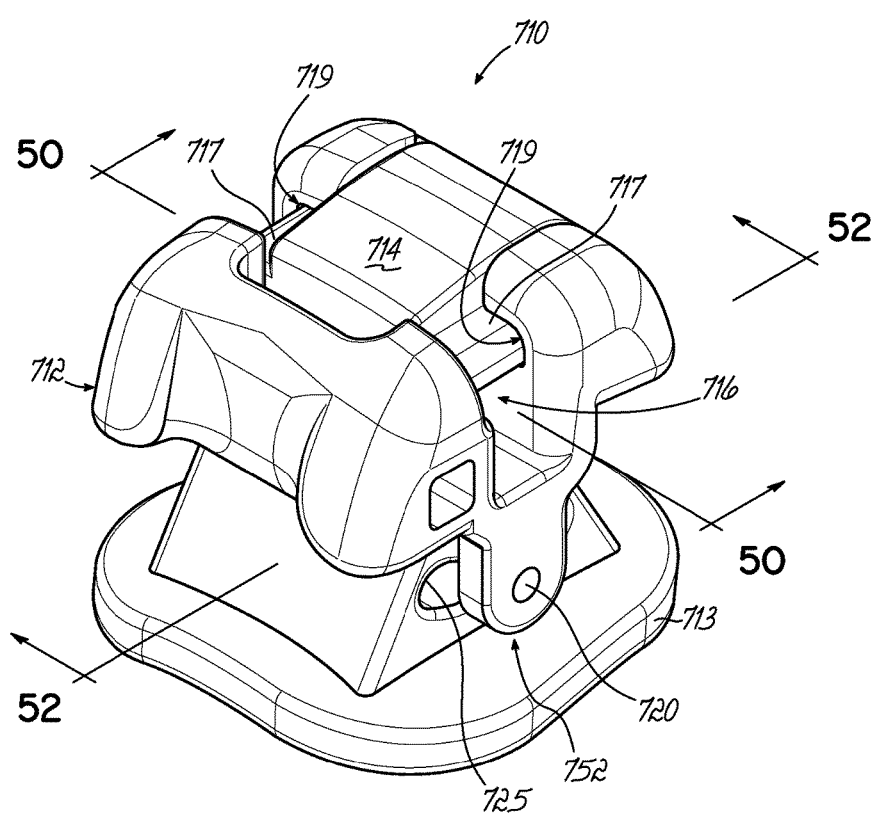
FIG. 49 is a perspective view of one embodiment of a self-ligating orthodontic bracket in accordance with the principles of the present invention.

In particular, the FSMA spring pin 620 extends from a fixed location through the rocker 621 into the retaining slot 625 of the track 623. In the exemplary embodiment shown, the track 623 has an arcuate shape that generally coincides with the contoured surfaces 618, 622 to define the motion of the bracket body 612 relative to the base member 613. With reference to FIGS. 46-48, the retaining slot 625 has enlarged portions 626 and straight portions 628. The retaining slot 625 forms a portion of the track 623.

The locking system 652 secures the bracket body 612 against relative movement to the base member 613. In this regard, the FSMA spring pin 620, when it is in its expanded state, is sized to be larger in diameter than the width dimension of the straight portions 628. By contrast, the enlarged portions 626 are sized to receive the spring pin 620 when the spring pin 620 is in the expanded state. Therefore, when the spring pin 620 resides in the enlarged portion 626 and is in its expanded state, there is an interference fit between the spring pin 620 and the straight portions 628. This configuration restricts relative movement between the bracket body 612 and the base member 613. The enlarged portions 626 therefore define a plurality of fixed, angular positions between the bracket body 612 and the base member 613.

The spring pin 620, however, slidably cooperates with the retaining slot 625 between locked positions or between the enlarged portions 626. To do so, the size of the spring pin 620 is retractable from the expanded state shown in FIG. 46 to a contracted state. In the contracted state, the straight portions 628 slidably receive the spring pin 620.

In operation, the clinician exposes the spring pin 620 to a magnetic field (B) or a magnetic field gradient that causes the spring pin 620 to contract as is shown in FIG. 47. In this contracted configuration, the clinician may pivot the base member 613 such that the rocker 621 rotates along the track 623 and the spring pin 620 slides in cooperation with the retaining slot 625, particularly in the straight portions 628, as shown in FIG. 47.

When the clinician has repositioned the base member 613 such that the spring pin 620 is aligned within an enlarged portion 626 of the retaining slot 625, the clinician may remove the magnetic field (B) or magnetic field gradient. The spring pin 620 may then expand into one enlarged portion 626 and lock the base member 613 in a new angular orientation, as shown in FIG. 48. The clinician may therefore operate the spring pin 620 even though it may not be accessible from the exterior of the bracket 610.

With reference now to FIGS. 49-54, in one embodiment, a self-ligating orthodontic bracket 710 includes a bracket body 712 and a movable member, such as, a ligating slide 714, coupled to the bracket body 712. The orthodontic bracket 710 includes a base member 713. The bracket body 712 is movable relative to the base member 713 similar to the orthodontic bracket 610 shown in FIG. 36. The bracket body 712 includes an archwire slot 716.

In the exemplary embodiment shown, the bracket body 712 and the base member 713 include complementary contoured portions 730, 732, respectively. To receive the ligating slide 714, the bracket body includes retainers 719. The clinician may pivot the bracket body 712 on the base member 713 by which the surfaces 730, 732 move relative to one another. The orthodontic bracket 710 may include a locking system 752, described below.

The ligating slide 714 includes rails 717 positioned within corresponding retainers 719 in the bracket body 712 and is movable between an opened position and a closed position in which the archwire is retained within the archwire slot 716. The ligating slide 714 may be movable with an FSMA actuator described below, as described above in conjunction with the embodiment shown in FIGS. 36-41.

In one embodiment, the locking system 752 secures the bracket body 712 relative to the base member 713 in predetermined fixed torque positions. The locking system 752 includes an FSMA actuator 720 fixed to one of the bracket body 712 and the base member 713 and a retaining slot 725 in the other of the bracket body 712 and the base member 713.

Figure 50:
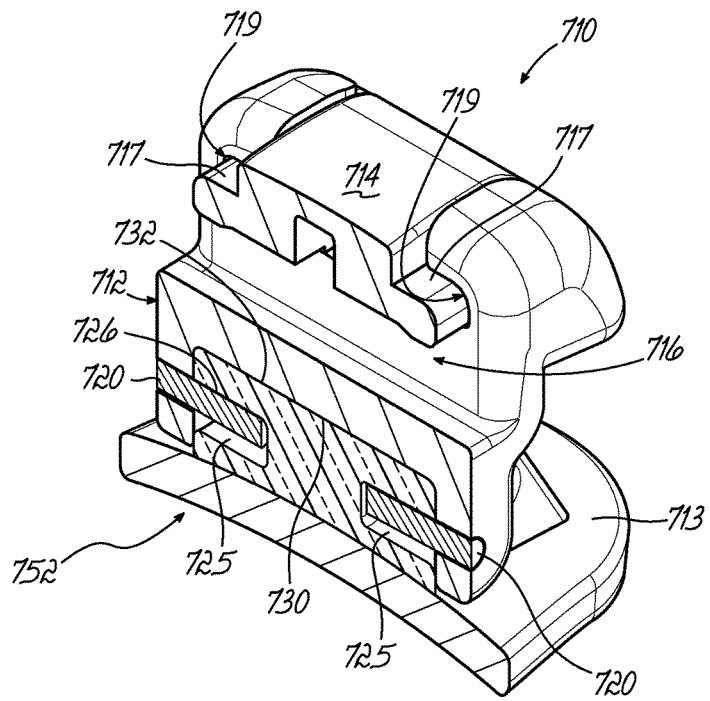
FIG. 50 is a cross-sectional view of the self-ligating orthodontic bracket of FIG. 49, taken along section line 50-50.
Figure 51:
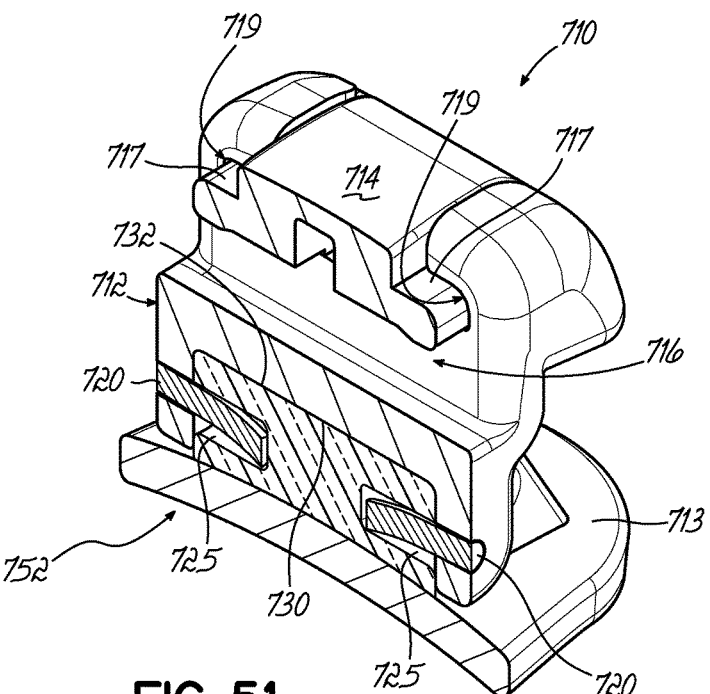
FIG. 51 is a cross-sectional view similar to FIG. 50, but showing displacement of actuator members.

In the exemplary embodiment shown in FIGS. 50 and 51, the FSMA actuator 720 is in the form of a pair of elongated pins or cylinders that are fixed to the bracket body 712. The elongated cylinders 720 move with the bracket body 712 relative to the base member 713 in cooperation with the retaining slot 725. It will be appreciated that while two elongated cylinders 720 are shown cooperating with two slots 725, only a single elongate cylinder 720 and a corresponding slot 725 may be needed to effectively lock the bracket body 712 relative to the base member 713.

Each of the elongated cylinders 720 has a straight configuration and a bent configuration for locking and unlocking, respectively, the bracket body 712 relative to the base member 713. One of the straight configuration and the bent configuration is a "normal" configuration and the other configuration is achieved by exposing the FSMA actuator to a magnetic field (B) or a magnetic field gradient. In the exemplary embodiment shown, the elongated cylinders 720 are normally straight and only when exposed to a magnetic field (B) or magnetic field gradient do the elongate cylinders 720 bend, as is shown in FIG. 51. It will be appreciated that the reverse arrangement is also contemplated. In other words, the elongate cylinders may be normally bent and only when exposed to a magnetic field (B) or a magnetic field gradient do the elongate cylinders 720 straighten.

Figure 52:
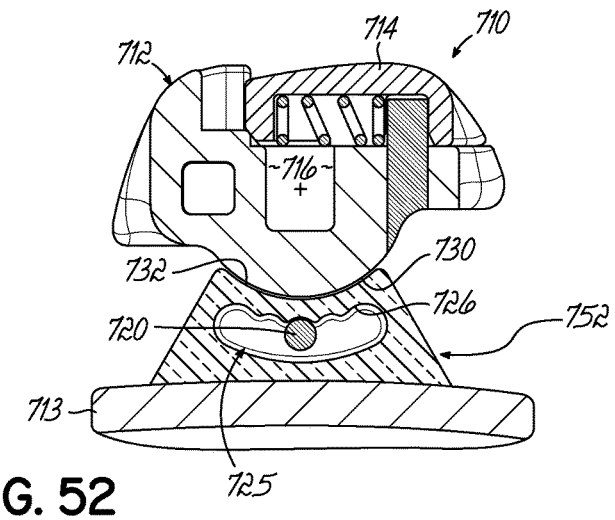
FIGS. 52-54 are cross-sectional views of the self-ligating orthodontic bracket of FIG. 49 taken along section line 52-52, with actuator members in various positions.
Figure 53:
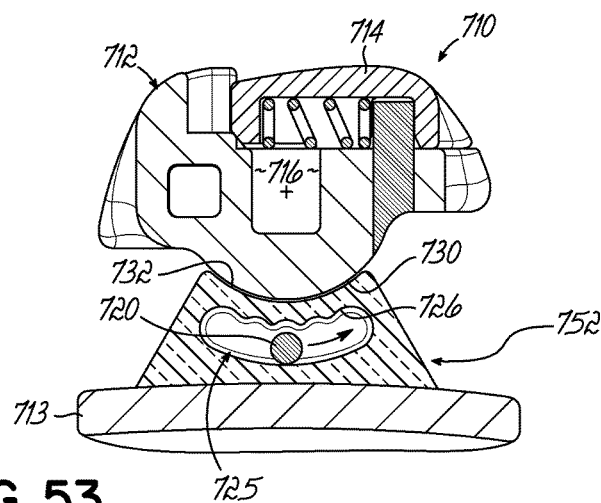
Figure 54:
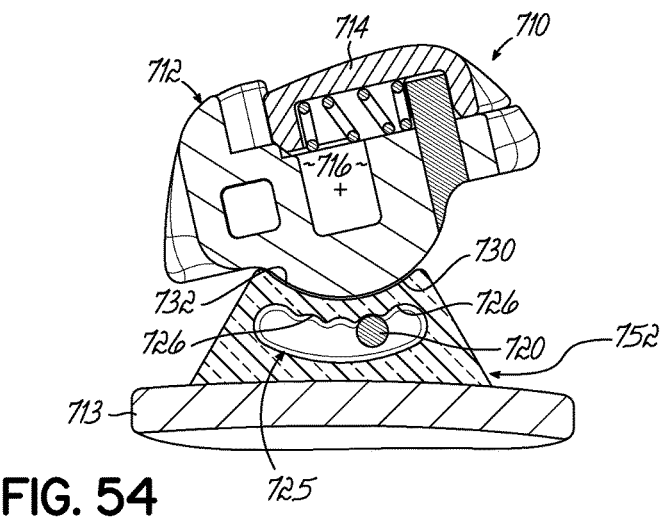

Further, in the exemplary embodiment shown, the retaining slot 725 has a saw tooth-like configuration with a series of spaced apart notches 726, as best shown in FIGS. 52-54. The retaining slot 725 is positioned lingually to the contoured portion of the base member 713, and the FSMA actuators 720 cooperate with the retaining slot 725 to reside in a corresponding one of the spaced apart notches 726 when the bracket body 712 is locked relative to the base member 713.

At this location, each of the elongated cylinders 720 is positioned in a corresponding notch 726. The notches 726 therefore interfere with sliding movement of the cylinders 720 in the retaining slot 725 when the cylinders 720 are straight. The locking system 752 therefore prohibits or at least resists movement between the bracket body 712 and the base member 713. To move the bracket body 712 to a different preselected fixed position, the clinician must first unlock the locking system 752.

To do so, the clinician exposes the cylindrical members 720 to a magnetic field (B) or a magnetic field gradient that causes the cylindrical members 720 to deflect or bend away from the corresponding notch 726. Once the cylindrical members 720 are clear of the notches 726, the clinician may then pivot the bracket body 712 relative to the base member 713. It will be appreciated that the clinician may continue to expose the cylindrical members 720 to the magnetic field (B) or the magnetic field gradient during movement to maintain the cylinders 720 in their deflected configuration. The cylindrical members 720 may slide in cooperation with the retaining slot 725, as shown in FIG. 53, as the bracket body 712 is moved.

When the clinician has repositioned the bracket body 712 and the cylindrical members 720 are each aligned within a corresponding notch 726 of the retaining slot 725, the clinician may remove the magnetic field (B) or the magnetic field gradient. The cylindrical members 720 then return to their normally straight configuration. In this way, the locking system 752 is re-engaged so that the bracket body 712 is secured to the base member 713, as shown in FIG. 54.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in any combination depending on the needs and preferences of the user.

What is claimed is:

1. A self-ligating orthodontic bracket for ligating an archwire comprising:
    a bracket body defining an archwire slot that is configured to receive the archwire;
    a movable member movable relative to the archwire slot; and
    an actuator coupled to at least one of the bracket body and the movable member, including a ferromagnetic shape memory alloy, and being configured to move the movable member when exposed to a magnetic field.

2. The orthodontic bracket of claim 1, wherein the ferromagnetic shape memory alloy is one of an iron-palladium (FePd) alloy, a nickel-manganese-gallium (NiMnGa) alloy, or a nickel-manganese-aluminum (NiMnAl) alloy.

3. The orthodontic bracket of claim 1, wherein the movable member is movable from an opened position to a closed position, and wherein the actuator is configured to move the movable member to the closed position or to the opened position when exposed to the magnetic field.

4. The orthodontic bracket of claim 1, wherein the actuator is coil spring shaped.

5. The orthodontic bracket of claim 1, wherein when exposed to the magnetic field, the actuator rotates or translates the movable member relative to the bracket body.

6. The orthodontic bracket of claim 1, further comprising a locking mechanism configured to secure the movable member in the closed position.

7. The orthodontic bracket of claim 1, wherein the movable member is a double door-like member.

8. A self-ligating orthodontic bracket for ligating an archwire comprising:
    a bracket body defining an archwire slot that is configured to receive the archwire; and
    a movable member coupled to the bracket body, including a ferromagnetic shape memory alloy, and moving relative to the archwire slot when exposed to a magnetic field from one of an opened position or a closed position to the other of the opened position or the closed position.

9. The orthodontic bracket of claim 8, wherein the movable member further includes a non-ferromagnetic shape memory alloy.

10. The orthodontic bracket of claim 9, wherein the shape memory alloy is one of a nickel-titanium (NiTi) alloy, copper-aluminum-nickel (CuAlNi) alloy, or a copper-aluminum-manganese (CuAlMn) alloy.

11. The orthodontic bracket of claim 8, wherein the movable member is a layered composite including at least one layer of the ferromagnetic shape memory alloy and at least one layer of a non-ferromagnetic shape memory alloy.

12. The orthodontic bracket of claim 11, wherein the movable member is a coiled door member including at least a coiled portion configured to uncoil and form a planar portion that extends at least partially across the archwire slot.

13. The orthodontic bracket of claim 12, wherein the movable member is configured to uncoil when exposed to a magnetic field.

14. The orthodontic bracket of claim 8, wherein the movable member has an L-shaped cross-sectional configuration, has a planar configuration, and is configured to change shape between the L-shaped cross-sectional configuration and the planar configuration when exposed to the magnetic field.

15. The orthodontic bracket of claim 8, wherein the movable member moves relative to the archwire slot when exposed to a magnetic field from the opened position to the closed position.

16. The orthodontic bracket of claim 8, wherein the movable member moves relative to the archwire slot when exposed to a magnetic field from the closed position to the opened position.

17. A self-ligating orthodontic bracket for ligating an archwire comprising:
    a bracket body defining an archwire slot that is configured to receive the archwire;
    a movable member coupled to the bracket body and movable relative to the archwire slot;
    a base member movably coupled to the bracket body; and
    a locking system for securing the bracket body relative to the base member and including a pin of a ferromagnetic shape memory alloy configured to change shape when exposed to a magnetic field.

18. The self-ligating orthodontic bracket of claim 17, wherein exposing the locking system to a magnetic field unlocks the locking system.

19. The self-ligating orthodontic bracket of claim 17, wherein the locking system further includes a retaining slot having a plurality of enlarged portions separated by straight portions, the enlarged portions corresponding to predetermined fixed orientations between the bracket body and the base member and the pin cooperates with a corresponding one of the enlarged portions for each predetermined fixed orientation.

20. The self-ligating orthodontic bracket of claim 19, wherein the predetermined fixed orientations correspond to predetermined torque positions.

21. The self-ligating orthodontic bracket of claim 17, wherein the locking system further includes a retaining slot having a plurality of spaced apart notches corresponding to predetermined fixed relative orientations between the bracket body and the base member and the pin cooperates with a corresponding one of the spaced apart notches for each predetermined fixed orientation.

22. A method of orthodontic treatment using a self-ligating orthodontic bracket having an archwire slot configured to receive an archwire therein and a movable member movable relative to the archwire slot, the orthodontic bracket including a ferromagnetic shape memory alloy, the method comprising:

exposing at least a portion of the orthodontic bracket to a magnetic field such that the ferromagnetic shape memory alloy at least partially transforms to a martensitic phase from an austenitic phase such that the movable member moves from one of an opened position or a closed position to the other of the opened position or the closed position; and inserting an archwire into and/or removing an archwire from the archwire slot.

23. The method of claim 22, wherein exposing includes positioning a device capable of producing a magnetic field proximate the orthodontic bracket prior to inserting or removing the archwire from the archwire slot.

24. The method of claim 22, wherein exposing the orthodontic bracket to the magnetic field causes movement of the movable member without contact with a tool.

25. A method of orthodontic treatment using a self-ligating orthodontic bracket having an archwire slot configured to receive an archwire therein and including a ferromagnetic shape memory alloy, the method comprising:

exposing at least a portion of the orthodontic bracket to a magnetic field such that the ferromagnetic shape memory alloy at least partially transforms to a martensitic phase from an austenitic phase; and manipulating the orthodontic bracket to change the torque on the tooth.

26. The method of claim 25, wherein the orthodontic bracket includes a bracket body pivotably coupled to a base member and wherein manipulating includes changing the angular orientation between the bracket body and the base member.

* * * * *